(12) United States Patent
Morriss et al.

(10) Patent No.: US 11,020,136 B2
(45) Date of Patent: Jun. 1, 2021

(54) DEFLECTABLE GUIDE CATHETERS AND RELATED METHODS

(71) Applicant: Acclarent, Inc., Irvine, CA (US)

(72) Inventors: John H. Morriss, Emerald Hills, CA (US); Joshua Makower, Los Altos, CA (US); Mei Pader, Fremont, CA (US); Julia D. Vrany, Los Altos, CA (US); Eric Goldfarb, Belmont, CA (US); Randy S. Chan, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 154 days.

(21) Appl. No.: 16/212,864

(22) Filed: Dec. 7, 2018

(65) Prior Publication Data

US 2019/0201017 A1  Jul. 4, 2019

Related U.S. Application Data

(63) Continuation of application No. 11/804,308, filed on May 16, 2007, now Pat. No. 10,188,413, which is a
(Continued)

(51) Int. Cl.
*A61B 17/24* (2006.01)
*A61M 25/01* (2006.01)
(Continued)

(52) U.S. Cl.
CPC ......... *A61B 17/24* (2013.01); *A61M 25/0147* (2013.01); *A61M 29/00* (2013.01);
(Continued)

(58) Field of Classification Search
CPC .............. A61B 17/24; A61B 2017/003; A61B 2017/00305; A61B 2017/00323;
(Continued)

(56) References Cited

U.S. PATENT DOCUMENTS

| 446,173 A | 2/1891 | Hancock |
| 504,424 A | 9/1893 | De Pezzer |

(Continued)

FOREIGN PATENT DOCUMENTS

| CA | 2013323 | 9/1990 |
| CH | 668188 | 12/1988 |

(Continued)

OTHER PUBLICATIONS

U.S. Appl. No. 10/829,917.
(Continued)

*Primary Examiner* — Richard G Louis
(74) *Attorney, Agent, or Firm* — Frost Brown Todd LLC

(57) ABSTRACT

Deflectable guide catheters and methods, including methods for using deflectable guide catheters to perform transnasal procedures within the ear, nose, throat, paranasal sinuses or cranium. Some deflectable guide catheters of the present invention comprise a substantially rigid tube, a helical spring attached to and extending from the distal end of the substantially rigid tube, a tubular plastic inner jacket, an outer plastic jacket substantially covering at least the helical spring member. The spring member is deflectable to cause the distal portion of the guide catheter to deflect to a curved configuration. In embodiments for transnasal use the deflectable guide catheter may have a length of less than 25 cm.

20 Claims, 6 Drawing Sheets

Related U.S. Application Data continuation-in-part of application No. 11/037,548, filed on Jan. 18, 2005, now Pat. No. 7,462,175, which is a continuation-in-part of application No. 10/829,917, filed on Apr. 21, 2004, now Pat. No. 7,654,997, said application No. 11/804,308 is a continuation-in-part of application No. 11/150,847, filed on Jun. 10, 2005, now Pat. No. 7,803,150, which is a continuation-in-part of application No. 10/944,270, filed on Sep. 17, 2004, now abandoned, which is a continuation-in-part of application No. 10/829,917, filed on Apr. 21, 2004, now Pat. No. 7,654,997, said application No. 11/804,308 is a continuation-in-part of application No. 11/193,020, filed on Jul. 29, 2005, now abandoned, which is a continuation-in-part of application No. 10/944,270, filed on Sep. 17, 2004, now abandoned, which is a continuation-in-part of application No. 10/829,917, filed on Apr. 21, 2004, now Pat. No. 7,654,997, said application No. 11/804,308 is a continuation-in-part of application No. 11/436,892, filed on May 17, 2006, now abandoned, which is a continuation-in-part of application No. 11/116,118, filed on Apr. 26, 2005, now Pat. No. 7,720,521, which is a continuation-in-part of application No. 10/829,917, filed on Apr. 21, 2004, now Pat. No. 7,654,997, said application No. 11/436,892 is a continuation-in-part of application No. 10/912,578, filed on Aug. 4, 2004, now Pat. No. 7,361,168, and a continuation-in-part of application No. 10/944,270, filed on Sep. 17, 2004, now abandoned, and a continuation-in-part of application No. 11/037,548, filed on Jan. 18, 2005, now Pat. No. 7,462,175.

(51) Int. Cl.
*A61M 29/00* (2006.01)
*A61M 25/00* (2006.01)
*A61B 17/00* (2006.01)
*A61B 17/34* (2006.01)
*A61B 90/00* (2016.01)
*A61M 25/06* (2006.01)

(52) U.S. Cl.
CPC .......... *A61B 2017/003* (2013.01); *A61B 2017/00305* (2013.01); *A61B 2017/00323* (2013.01); *A61B 2017/00455* (2013.01); *A61B 2017/3447* (2013.01); *A61B 2090/0811* (2016.02); *A61B 2090/3614* (2016.02); *A61M 25/005* (2013.01); *A61M 25/0052* (2013.01); *A61M 25/0152* (2013.01); *A61M 25/0155* (2013.01); *A61M 25/0158* (2013.01); *A61M 25/0662* (2013.01); *A61M 2025/015* (2013.01); *A61M 2025/0161* (2013.01); *A61M 2025/0166* (2013.01); *A61M 2210/0618* (2013.01); *A61M 2210/0681* (2013.01)

(58) Field of Classification Search
CPC .. A61B 2017/00455; A61B 2090/3614; A61B 2090/0811; A61M 29/00; A61M 25/0147; A61M 25/0052; A61M 25/0662; A61M 2025/0161; A61M 25/005; A61M 2210/0681; A61M 25/0158; A61M 2210/0618
See application file for complete search history.

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,477,438 A | 11/1969 | Allen et al. |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,137 A | 6/1970 | Santomieri |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |

(56) References Cited

U.S. PATENT DOCUMENTS

| | | |
|---|---|---|
| 4,311,146 A | 1/1982 | Wonder |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,441,495 A | 4/1984 | Hicswa |
| 4,467,790 A | 4/1984 | Schiff |
| 4,445,892 A | 5/1984 | Hussein et al. |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,517,979 A | 5/1985 | Pecenka |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,592,357 A | 6/1986 | Ersek |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,641,654 A | 2/1987 | Samson et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,682,607 A | 7/1987 | Vaillancourt et al. |
| 4,684,363 A | 8/1987 | Ari et al. |
| 4,686,965 A | 8/1987 | Bonnet et al. |
| 4,691,948 A | 9/1987 | Austin, Jr. et al. |
| 4,696,544 A | 9/1987 | Costella |
| 4,700,694 A | 10/1987 | Shishido |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,753,637 A | 6/1988 | Horneffer |
| 4,755,171 A | 7/1988 | Tennant |
| 4,771,776 A | 9/1988 | Powell et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,802,461 A | 2/1989 | Cho |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,834,709 A | 5/1989 | Banning et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,953,553 A | 9/1990 | Tremulis |
| 4,961,433 A | 10/1990 | Christian |
| 4,966,163 A | 10/1990 | Kraus et al. |
| 4,984,581 A | 1/1991 | Stice |
| 4,986,810 A | 1/1991 | Semrad |
| 4,991,588 A | 2/1991 | Pflueger et al. |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,040,548 A | 8/1991 | Yock |
| 5,041,089 A | 8/1991 | Mueller et al. |
| 5,044,678 A | 9/1991 | Detweiler |
| 5,049,132 A | 9/1991 | Shaffer et al. |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | Lind |
| 5,069,226 A | 12/1991 | Tamauchi et al. |
| 5,084,010 A | 1/1992 | Plaia et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,090,959 A | 2/1992 | Samson et al. |
| 5,099,845 A | 3/1992 | Besz et al. |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,161,534 A | 11/1992 | Berthiaume |
| 5,163,989 A | 11/1992 | Campbell et al. |
| 5,165,420 A | 11/1992 | Strickland |
| 5,167,220 A | 12/1992 | Brown |
| 5,168,864 A | 12/1992 | Skockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,195,971 A | 3/1993 | Sirhan |
| 5,197,457 A | 3/1993 | Adair |
| 5,201,908 A | 4/1993 | Jones |
| 5,207,695 A | 5/1993 | Trout, III |
| 5,211,952 A | 5/1993 | Spicer et al. |
| 5,213,576 A | 5/1993 | Abiuso et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |

(56) References Cited

U.S. PATENT DOCUMENTS

| | | |
|---|---|---|
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,292,305 A | 3/1994 | Boudewijn et al. |
| 5,295,694 A | 3/1994 | Levin |
| 5,300,085 A | 4/1994 | Yock |
| 5,304,123 A | 4/1994 | Atala et al. |
| 5,306,272 A | 4/1994 | Cohen et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,314,443 A | 5/1994 | Rudnick |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,143 A | 8/1994 | Carroll |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,370,640 A | 12/1994 | Kolff |
| 5,372,138 A | 12/1994 | Crowley et al. |
| 5,372,584 A | 12/1994 | Zink et al. |
| D355,031 S | 1/1995 | Yoshikawa |
| 5,378,234 A * | 1/1995 | Hammerslag ..... A61M 25/0053 138/129 |
| 5,385,562 A | 1/1995 | Adams et al. |
| 5,386,817 A | 2/1995 | Jones |
| 5,386,828 A | 2/1995 | Owens et al. |
| 5,391,147 A | 2/1995 | Imran et al. |
| 5,391,179 A | 2/1995 | Mezzoli |
| 5,395,367 A | 3/1995 | Wilk |
| 5,397,305 A | 3/1995 | Kawula et al. |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,483 A | 8/1995 | Avitall |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,309 A | 12/1995 | Sweezer et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,653,690 A | 8/1997 | Booth et al. |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,720,719 A | 2/1998 | Edwards et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,749,357 A | 5/1998 | Linder |
| 5,749,920 A | 5/1998 | Quiachon et al. |
| 5,752,513 A | 5/1998 | Acker et al. |
| 5,752,971 A | 5/1998 | Rosenbluth et al. |

(56) References Cited

U.S. PATENT DOCUMENTS

| | | |
|---|---|---|
| 5,762,604 A | 6/1998 | Kieturakis |
| 5,766,158 A | 6/1998 | Opolski |
| 5,769,821 A | 6/1998 | Abrahamson et al. |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,823,961 A | 10/1998 | Fields et al. |
| 5,824,044 A | 10/1998 | Quiachon et al. |
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,827,323 A | 10/1998 | Klieman et al. |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,836,951 A | 11/1998 | Rosenbluth et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,882,333 A | 3/1999 | Schaer et al. |
| 5,882,346 A | 3/1999 | Pomeranz et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,916,213 A | 6/1999 | Haissaguerre et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| 5,941,849 A | 8/1999 | Amos, Jr. et al. |
| D413,629 S | 9/1999 | Wolff |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,967,984 A | 10/1999 | Chu et al. |
| 5,968,085 A | 10/1999 | Morris et al. |
| 5,971,975 A | 10/1999 | Mills et al. |
| 5,976,074 A | 11/1999 | Moriyama |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,989,025 A | 11/1999 | Conley |
| 5,993,462 A | 11/1999 | Pomeranz et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,022 A | 5/2000 | Ben-Haim |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,102,891 A | 8/2000 | van Erp et al. |
| 6,109,268 A | 8/2000 | Thapliyal et al. |
| 6,113,567 A | 9/2000 | becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,402 A | 11/2000 | Munoz |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,776 B1 | 1/2001 | Adams et al. |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,238,430 B1 | 5/2001 | Klumb et al. |
| 6,241,519 B1 | 6/2001 | Sedleemayer |
| 6,248,092 B1 | 6/2001 | Miraki et al. |
| 6,249,180 B1 | 6/2001 | Maalej et al. |
| 6,254,550 B1 | 7/2001 | McNamara et al. |
| 6,264,087 B1 | 7/2001 | Whitman |
| 6,268,574 B1 | 7/2001 | Edens |
| 6,270,477 B1 | 8/2001 | Bagaoisan et al. |
| 6,280,433 B1 | 8/2001 | McIvor et al. |

(56) References Cited

U.S. PATENT DOCUMENTS

| | | |
|---|---|---|
| 6,283,908 B1 | 8/2001 | Aviram et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,304,768 B1 | 10/2001 | Blume et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,328,730 B1 | 12/2001 | Harkrider, Jr. |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,379,319 B1 | 4/2002 | Garibotto et al. |
| 6,381,485 B1 | 4/2002 | Hunter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,436,119 B1 | 8/2002 | Erb et al. |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,520,954 B2 | 2/2003 | Ouchi |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,530,897 B2 * | 3/2003 | Nardeo ............... A61M 25/008 600/146 |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,562,022 B2 | 5/2003 | Hoste et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B1 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,645,223 B2 | 11/2003 | Boyle et al. |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,833 B2 | 1/2004 | Smith et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,740,191 B2 | 5/2004 | Clarke et al. |
| 6,741,884 B1 | 5/2004 | Freeman et al. |
| 6,743,168 B2 | 6/2004 | Luloh et al. |
| 6,755,812 B2 | 6/2004 | Peterson et al. |
| 6,758,857 B2 | 7/2004 | Cioanta et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,866,669 B2 | 3/2005 | Buzzard et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |

(56) References Cited

U.S. PATENT DOCUMENTS

| | | |
|---|---|---|
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,953,431 B2 | 10/2005 | Barthel |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,979,979 B2 | 12/2005 | Xu et al. |
| 6,984,203 B2 | 1/2006 | Tartaglia et al. |
| 6,989,024 B2 | 1/2006 | Hebert et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,004,176 B2 | 2/2006 | Lau |
| 7,008,412 B2 | 3/2006 | Maginot |
| 7,011,654 B2 | 3/2006 | Dubrul et al. |
| 7,022,105 B1 | 4/2006 | Edwards |
| 7,037,321 B2 | 5/2006 | Sachdeva |
| 7,043,961 B2 | 5/2006 | Pandey |
| 7,044,964 B2 | 5/2006 | Jang et al. |
| 7,048,711 B2 | 5/2006 | Rosenmann et al. |
| 7,052,474 B2 | 5/2006 | Castell et al. |
| 7,056,284 B2 | 6/2006 | Martone et al. |
| 7,056,287 B2 | 6/2006 | Taylor et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,186,224 B2 | 3/2007 | Windheuser |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,248,914 B2 | 7/2007 | Hastings et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,309,334 B2 | 12/2007 | von Hoffmann |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,384,407 B2 | 6/2008 | Rodriguez et al. |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,551,758 B2 | 6/2009 | Florent et al. |
| 7,559,925 B2 | 7/2009 | Goldfarb et al. |
| 7,566,300 B2 | 7/2009 | Devierre et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,697,972 B2 | 4/2010 | Verard et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,751,758 B2 | 7/2010 | Yahagi |
| 7,753,929 B2 | 7/2010 | Becker |
| 7,753,930 B2 | 7/2010 | Becker |
| 7,758,497 B2 | 7/2010 | Hern |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| 7,857,750 B2 | 12/2010 | Belafsky |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,927,271 B2 | 4/2011 | Dimitriou et al. |
| 7,951,132 B2 | 5/2011 | Eaton et al. |
| 7,988,705 B2 | 8/2011 | Galdonik et al. |
| 7,993,353 B2 | 8/2011 | Roßner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,075,476 B2 | 12/2011 | Vargas |
| 8,075,478 B2 | 12/2011 | Campos |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |

(56) References Cited

U.S. PATENT DOCUMENTS

| | | | |
|---|---|---|---|
| 8,100,933 B2 | 1/2012 | Becker | |
| 8,104,483 B2 | 1/2012 | Taylor | |
| 8,114,062 B2 | 2/2012 | Muni et al. | |
| 8,114,113 B2 | 2/2012 | Becker | |
| 8,123,722 B2 | 2/2012 | Chang et al. | |
| 8,142,422 B2 | 3/2012 | Makower et al. | |
| 8,146,400 B2 | 4/2012 | Goldfarb et al. | |
| 8,147,545 B2 | 4/2012 | Avior | |
| 8,167,821 B2 | 5/2012 | Sharrow | |
| 8,172,828 B2 | 5/2012 | Chang et al. | |
| 8,190,389 B2 | 5/2012 | Kim et al. | |
| 8,197,433 B2 | 6/2012 | Cohen | |
| 8,197,552 B2 | 6/2012 | Mandpe | |
| 8,249,700 B2 | 8/2012 | Clifford et al. | |
| 8,277,386 B2 | 10/2012 | Ahmed et al. | |
| 8,317,816 B2 | 11/2012 | Becker | |
| 8,337,454 B2 | 12/2012 | Eaton et al. | |
| 8,388,642 B2 | 3/2013 | Muni et al. | |
| 8,403,954 B2 | 3/2013 | Santin et al. | |
| 8,414,473 B2 | 4/2013 | Jenkins et al. | |
| 8,425,457 B2 | 4/2013 | John et al. | |
| 8,439,687 B1 | 5/2013 | Morriss et al. | |
| 8,475,360 B2 | 7/2013 | Brown | |
| 8,521,259 B2 | 8/2013 | Mandrusov et al. | |
| 8,529,439 B2 | 9/2013 | Ito et al. | |
| 8,535,707 B2 | 9/2013 | Arensdorf et al. | |
| 8,568,439 B2 | 10/2013 | Keith et al. | |
| 8,702,626 B1 | 4/2014 | Kim et al. | |
| 8,715,169 B2 | 5/2014 | Chang et al. | |
| 8,721,591 B2 | 5/2014 | Chang et al. | |
| 8,740,292 B2 | 6/2014 | Gopferich et al. | |
| 8,740,839 B2 | 6/2014 | Eaton et al. | |
| 8,747,389 B2 | 6/2014 | Goldfarb et al. | |
| 8,764,709 B2 | 7/2014 | Chang et al. | |
| 8,764,726 B2 | 7/2014 | Chang et al. | |
| 8,764,729 B2 | 7/2014 | Muni et al. | |
| 8,777,926 B2 | 7/2014 | Chang et al. | |
| 8,802,131 B2 | 8/2014 | Arensdorf et al. | |
| 8,828,041 B2 | 9/2014 | Chang et al. | |
| 9,101,574 B2 | 8/2015 | Chang et al. | |
| 9,220,879 B2 | 12/2015 | Chang et al. | |
| 9,241,834 B2 | 1/2016 | Chang et al. | |
| 9,370,649 B2 | 6/2016 | Chang et al. | |
| 9,399,121 B2 | 7/2016 | Goldfarb et al. | |
| 9,610,428 B2 | 4/2017 | Muni et al. | |
| 9,649,477 B2 | 5/2017 | Muni et al. | |
| 10,098,652 B2 | 10/2018 | Goldfarb et al. | |
| 10,124,154 B2 | 11/2018 | Evard et al. | |
| 10,188,413 B1 | 1/2019 | Morriss et al. | |
| 2001/0004644 A1 | 6/2001 | Levin | |
| 2001/0005785 A1 | 6/2001 | Sachse | |
| 2001/0027310 A1* | 10/2001 | Parisi | A61L 29/12 604/524 |
| 2001/0034530 A1 | 10/2001 | Malackowski et al. | |
| 2001/0037084 A1 | 11/2001 | Nardeo | |
| 2002/0006961 A1 | 1/2002 | Katz et al. | |
| 2002/0013548 A1 | 1/2002 | Hinchliffe | |
| 2002/0055746 A1 | 5/2002 | Burke et al. | |
| 2002/0068851 A1 | 6/2002 | Gravenstein et al. | |
| 2002/0077593 A1 | 6/2002 | Perkins et al. | |
| 2002/0090388 A1 | 7/2002 | Humes et al. | |
| 2002/0115963 A1 | 8/2002 | Clarke et al. | |
| 2002/0161389 A1 | 10/2002 | Boyle et al. | |
| 2003/0009095 A1 | 1/2003 | Skarda | |
| 2003/0013985 A1 | 1/2003 | Saadat | |
| 2003/0017111 A1 | 1/2003 | Rabito | |
| 2003/0018291 A1 | 1/2003 | Hill et al. | |
| 2003/0040697 A1 | 2/2003 | Pass et al. | |
| 2003/0051733 A1 | 3/2003 | Kotmel et al. | |
| 2003/0073900 A1 | 4/2003 | Senarith et al. | |
| 2003/0074045 A1 | 4/2003 | Buzzard et al. | |
| 2003/0083608 A1 | 5/2003 | Evans et al. | |
| 2003/0114732 A1 | 6/2003 | Webler et al. | |
| 2003/0163154 A1 | 8/2003 | Miyata et al. | |
| 2003/0220551 A1 | 11/2003 | Kimball et al. | |
| 2004/0015150 A1 | 1/2004 | Zadno-Azizi | |
| 2004/0018980 A1 | 1/2004 | Gurney et al. | |
| 2004/0020492 A1 | 2/2004 | Dubrul et al. | |
| 2004/0034311 A1 | 2/2004 | Mihakcik | |
| 2004/0043052 A1 | 3/2004 | Hunter et al. | |
| 2004/0058992 A1 | 3/2004 | Marinello et al. | |
| 2004/0064105 A1 | 4/2004 | Capes et al. | |
| 2004/0064150 A1 | 4/2004 | Becker | |
| 2004/0116958 A1 | 6/2004 | Gopferich et al. | |
| 2004/0127820 A1 | 7/2004 | Clayman et al. | |
| 2004/0148035 A1* | 7/2004 | Barrett | A61B 17/12104 623/23.65 |
| 2004/0158229 A1 | 8/2004 | Quinn | |
| 2004/0181175 A1 | 9/2004 | Clayman et al. | |
| 2004/0193073 A1 | 9/2004 | DeMello et al. | |
| 2004/0199052 A1* | 10/2004 | Banik | A61B 1/008 600/142 |
| 2004/0220516 A1 | 11/2004 | Solomon et al. | |
| 2004/0230156 A1 | 11/2004 | Schreck et al. | |
| 2004/0236231 A1 | 11/2004 | Knighton et al. | |
| 2004/0249243 A1 | 12/2004 | Kleiner | |
| 2004/0267347 A1 | 12/2004 | Cervantes | |
| 2005/0027249 A1 | 2/2005 | Reifart et al. | |
| 2005/0038319 A1 | 2/2005 | Goldwasser et al. | |
| 2005/0055077 A1 | 3/2005 | Marco | |
| 2005/0059930 A1 | 3/2005 | Garrison et al. | |
| 2005/0059931 A1 | 3/2005 | Garrison et al. | |
| 2005/0089670 A1 | 4/2005 | Large | |
| 2005/0107738 A1 | 5/2005 | Slater et al. | |
| 2005/0113687 A1 | 5/2005 | Herweck et al. | |
| 2005/0113850 A1 | 5/2005 | Tagge | |
| 2005/0119590 A1 | 6/2005 | Burmeister et al. | |
| 2005/0124856 A1 | 6/2005 | Fujikura et al. | |
| 2005/0131316 A1 | 6/2005 | Flagle et al. | |
| 2005/0143687 A1 | 6/2005 | Rosenblatt et al. | |
| 2005/0182319 A1 | 8/2005 | Glossop | |
| 2005/0228224 A1 | 10/2005 | Okada et al. | |
| 2005/0234507 A1 | 10/2005 | Geske et al. | |
| 2005/0240120 A1 | 10/2005 | Modesitt | |
| 2005/0244472 A1 | 11/2005 | Hughes et al. | |
| 2005/0283221 A1 | 12/2005 | Mann et al. | |
| 2006/0004323 A1 | 1/2006 | Chang et al. | |
| 2006/0047261 A1 | 3/2006 | Joshi | |
| 2006/0063973 A1 | 3/2006 | Makower et al. | |
| 2006/0173382 A1 | 8/2006 | Schreiner | |
| 2006/0189844 A1 | 8/2006 | Tien | |
| 2006/0190022 A1 | 8/2006 | Beyar et al. | |
| 2006/0211752 A1 | 9/2006 | Kohn et al. | |
| 2006/0271024 A1 | 11/2006 | Gertner et al. | |
| 2006/0284428 A1 | 12/2006 | Beadle et al. | |
| 2007/0020196 A1 | 1/2007 | Pipkin et al. | |
| 2007/0112358 A1 | 5/2007 | Abbott | |
| 2007/0129751 A1* | 6/2007 | Muni | A61B 17/24 606/196 |
| 2007/0135789 A1 | 6/2007 | Chang et al. | |
| 2007/0167682 A1 | 7/2007 | Goldfarb et al. | |
| 2007/0207186 A1 | 9/2007 | Scanlon et al. | |
| 2007/0208252 A1 | 9/2007 | Makower | |
| 2007/0208301 A1 | 9/2007 | Evard et al. | |
| 2007/0249896 A1 | 10/2007 | Goldfarb et al. | |
| 2007/0250105 A1 | 10/2007 | Ressemann et al. | |
| 2007/0269385 A1 | 11/2007 | Yun et al. | |
| 2007/0282305 A1 | 12/2007 | Goldfarb et al. | |
| 2007/0293727 A1 | 12/2007 | Goldfarb et al. | |
| 2007/0293946 A1 | 12/2007 | Gonzales et al. | |
| 2008/0015544 A1 | 1/2008 | Keith et al. | |
| 2008/0033519 A1 | 2/2008 | Burwell et al. | |
| 2008/0051804 A1 | 2/2008 | Cottler et al. | |
| 2008/0097516 A1 | 4/2008 | Chang et al. | |
| 2008/0103521 A1 | 5/2008 | Makower et al. | |
| 2008/0119693 A1 | 5/2008 | Makower et al. | |
| 2008/0132938 A1 | 6/2008 | Chang et al. | |
| 2008/0172033 A1 | 7/2008 | Keith et al. | |
| 2008/0183128 A1 | 7/2008 | Morriss et al. | |
| 2008/0188803 A1 | 8/2008 | Jang | |
| 2008/0188870 A1 | 8/2008 | Andre et al. | |
| 2008/0228085 A1 | 9/2008 | Jenkins et al. | |
| 2008/0262508 A1 | 10/2008 | Clifford et al. | |
| 2008/0275483 A1 | 11/2008 | Makower et al. | |

(56) References Cited

U.S. PATENT DOCUMENTS

| | | |
|---|---|---|
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0087811 A1 | 4/2010 | Herrin et al. |
| 2010/0114066 A1 | 5/2010 | Makower et al. |
| 2010/0174138 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0211007 A1 | 8/2010 | Lesch, Jr. et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | Chang et al. |
| 2013/0261388 A1 | 10/2013 | Jenkins et al. |
| 2014/0200444 A1 | 7/2014 | Kim et al. |
| 2014/0296898 A1 | 10/2014 | Chang et al. |
| 2014/0330074 A1 | 11/2014 | Morriss et al. |
| 2014/0336575 A1 | 11/2014 | Muni et al. |
| 2014/0336693 A1 | 11/2014 | Goldfarb et al. |
| 2014/0350465 A1 | 11/2014 | Muni et al. |
| 2014/0364725 A1 | 12/2014 | Makower |
| 2015/0088188 A1 | 3/2015 | Muni et al. |
| 2015/0165175 A1 | 6/2015 | Evard et al. |
| 2015/0165176 A1 | 6/2015 | Makower et al. |
| 2015/0182735 A1 | 7/2015 | Chang et al. |
| 2015/0209055 A1 | 7/2015 | Chang et al. |
| 2015/0250992 A1 | 9/2015 | Morriss et al. |
| 2016/0192830 A1 | 7/2016 | Goldfarb et al. |
| 2016/0270863 A1 | 9/2016 | Makower |
| 2017/0007281 A1 | 1/2017 | Goldfarb et al. |
| 2017/0071625 A1 | 3/2017 | Chang et al. |

FOREIGN PATENT DOCUMENTS

| | | |
|---|---|---|
| CN | 2151720 | 1/1994 |
| CN | 2352818 | 12/1999 |
| CN | 201005758 Y | 1/2008 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1112103 | 7/2001 |
| EP | 1166710 | 1/2002 |
| EP | 1413258 | 4/2004 |
| EP | 1944053 | 7/2008 |
| FR | 2662083 | 11/1991 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | S61-16750 | 1/1986 |
| JP | 10-24098 | 1/1989 |
| JP | H10-034376 | 2/1989 |
| JP | H01-305965 | 12/1989 |
| JP | 3-503011 | 7/1991 |
| JP | 3-504935 | 10/1991 |
| JP | 4-221313 | 8/1992 |
| JP | 4-224766 | 8/1992 |
| JP | H5-503650 | 6/1993 |
| JP | 5-211985 | 8/1993 |
| JP | H05-506805 | 10/1993 |
| JP | H06-017751 | 3/1994 |
| JP | 6-277296 | 10/1994 |
| JP | 7-327916 | 12/1995 |
| JP | 8-317989 | 12/1996 |
| JP | H10-501159 | 2/1998 |
| JP | H10-094543 | 4/1998 |
| JP | 11-507251 | 6/1999 |
| JP | 2000-501634 | 2/2000 |
| JP | 2000-126303 | 5/2000 |
| JP | 2001-025508 | 1/2001 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 2004-357728 | 12/2004 |
| JP | 2005-323702 | 11/2005 |
| JP | 2005-532869 | 11/2005 |
| JP | 2008-539031 | 11/2008 |
| RU | 2108764 | 4/1998 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 94/021320 | 9/1994 |
| WO | WO 95/002430 | 1/1995 |
| WO | WO 96/029071 | 9/1996 |
| WO | WO 97/021461 | 6/1997 |
| WO | WO 98/055174 | 12/1998 |
| WO | WO 99/000064 | 1/1999 |
| WO | WO 99/024106 | 5/1999 |
| WO | WO 99/026692 | 6/1999 |
| WO | WO 99/030655 | 6/1999 |
| WO | WO 99/032041 | 7/1999 |
| WO | WO 99/059649 | 11/1999 |
| WO | WO 00/009190 | 2/2000 |
| WO | WO 00/009192 | 2/2000 |
| WO | WO 00/023009 | 4/2000 |
| WO | WO 00/051672 | 9/2000 |
| WO | WO 00/053252 | 9/2000 |

(56) References Cited

FOREIGN PATENT DOCUMENTS

| | | |
|---|---|---|
| WO | WO 00/067834 | 11/2000 |
| WO | WO 01/005462 | 1/2001 |
| WO | WO 01/045572 | 6/2001 |
| WO | WO 01/054558 | 8/2001 |
| WO | WO 01/056481 | 8/2001 |
| WO | WO 01/068178 | 9/2001 |
| WO | WO 01/070325 | 9/2001 |
| WO | WO 01/082800 | 11/2001 |
| WO | WO 01/097895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/045387 | 6/2004 |
| WO | WO 04/058045 | 7/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/034203 | 3/2007 |
| WO | WO 07/035204 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |
| WO | WO 01/074266 | 10/2011 |

OTHER PUBLICATIONS

U.S. Appl. No. 10/912,557.
U.S. Appl. No. 10/912,587.
U.S. Appl. No. 10/944,270.
U.S. Appl. No. 11/037,548.
U.S. Appl. No. 11/116,118.
U.S. Appl. No. 11/150,847.
U.S. Appl. No. 11/193,020.
U.S. Appl. No. 11/355,512.
U.S. Appl. No. 11/436,892.
U.S. Appl. No. 11/647,530.
U.S. Appl. No. 11/789,704.
U.S. Appl. No. 11/789,705.
U.S. Appl. No. 11/803,695.
U.S. Appl. No. 11/804,308.
U.S. Appl. No. 11/929,667.
U.S. Appl. No. 12/184,166.
U.S. Appl. No. 12/496,226.
U.S. Appl. No. 12/639,919.
U.S. Appl. No. 12/649,027.
U.S. Appl. No. 12/793,352.
U.S. Appl. No. 12/949,708.
U.S. Appl. No. 13/301,406.
U.S. Appl. No. 13/451,453.
U.S. Appl. No. 13/858,580.
U.S. Appl. No. 13/867,972.
U.S. Appl. No. 14/221,550.
U.S. Appl. No. 14/221,714.
U.S. Appl. No. 14/265,787.
U.S. Appl. No. 14/265,888.
U.S. Appl. No. 14/266,002.
U.S. Appl. No. 14/327,593.
U.S. Appl. No. 14/464,948.
U.S. Appl. No. 14/515,687.
U.S. Appl. No. 14/566,845.
U.S. Appl. No. 14/567,051.
U.S. Appl. No. 14/614,799.
U.S. Appl. No. 14/658,432.
U.S. Appl. No. 14/993,444.
U.S. Appl. No. 15/083,826.
U.S. Appl. No. 15/187,938.
Argon Medical. Maxxim Medical. Ad for Sniper EliteTM Hydrophilic Ni-Ti Alloy Guidewire (2001).
Aust, R., et al. 'The Functional Size of the Human Maxillary Ostium in Vivo' Acta. Otolaryn. (9178) vol. 782 pp. 432-435.
Balm, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congenital Posterior Choanal Atresia' J. Larynsol. Otol (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. www.inventors.about.com/library/inventors/blcatheter.htm?p=1.
Benninger et al.; Adult Chronic Rhinosinusitis: Definitions, Diagnosis, Epidemiology, and Pathophysiology Arch Otolaryngology Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: The University of Miami Experience' American Journal of Rhinology, vol. 12 No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, pp. 60-63.
Cohen et al. 'Endoscopic Sinus Surgery: Where we are and where we're going' Current Opinion in Otolaamplogy & Head and Neck Surgery, vol. 13 (2005) pp. 32-38.
Colla, A. et al., 'Trihaloacetylated Enol Ethers-General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1 pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngology Head Neck Surg. vol. 129 (Apr. 2003) pp. 472-474.
Deutschniann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolgympl Head Neck Surg. vol. 2 (1991) pp. 234-240.

(56) References Cited

OTHER PUBLICATIONS

Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1999) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Lagnoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fling, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Larngoscope. vol. 18 (1908) pp. 266-274.
Gopferich 'Polymer Degradation and Erosion: Mechanisms and Application' Eur. J. Parm Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' 1 CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., 'Balloon Dilatation of Recurrent Ostial Occlusion of the Front Sinus' OASIS-Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Surgery and Hand Surgery (1999) vol. 33 pp. 321-324.
Hojo, M. et al, 'Electrophilic Substitutions of Olefinic Hydrogens II. Acylation of Vinyl Ethers and N Vinyl Amides Chemistry Letters' (1976) pp. 499-502. Chemical Society of Japan.
Hopf, J.U.G. et al. 'Miniature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 11 (1997) pp. 1-9.

Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1, 1999) www.brooksidepress.org/products/Operationa.Medicine/DATA. 2001 pp. 1-6.
Hybels, R.L. 'Transillumination During Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989). vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by T B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629
Kingdom, T.T. et al. 'Image-Guided Surgery of the Sinuses: Current Technology and Applications' Otolagngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. 1995 vol. 6, No. 5 pp. 711-713.
Lanza, D.C. 'Postoperative Care and Avoiding Frontal Recess Stenosis' Internatinal Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971). vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-492.

(56) References Cited

OTHER PUBLICATIONS

Medtronic, xomed.com-MicroFrance Catalog Browser. www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters'Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxillary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Park, K. et al. 'Biodegradable Hydrogels for Drug Delivery' (1993) Technomic Publishing Inc. Lancaster.
Piccirillo, J.F. et al. 'Psychometric and Clinometric Validity of the 20-Item Sino-Nasal Outcome test (SNOT-20)' Copyright 1996 Washington University, St. Louis, MO.
Piers, et al. 'A Flexible Distal Tip with Two Degrees of Freedom for Enhanced Dexterity in Endoscopic Robot Surgery' Proceedings 13th Micromechanics Europe Workshop (2002) pp. 271-274.
Podshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluoroscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].

Shah, N.J. et al., 'Endoscopic Pituitary Surgery—A Beginner's Guide' Indian Journal of Otolaryngology and Head and Neck Surgery (2004) vol. 56, No. 1. pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitenment Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn-Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993). Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steroid Distribution' Rhinology. vol. 37 (1999) pp. 69-73.
Weiner, R.I., D.O., et al., 'Development and Application of Trans Septal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low-Profile Monorail Balloon Catheter' Cathet. Cardiovasc. Diagn. (1994) vol. 33, No. 1, pp. 76-79.

(56) References Cited

OTHER PUBLICATIONS

Australian Office Action, Examiners First Report dated Apr. 8, 2010 for Application No. AU 2005274794.
Australian Office Action, Examiners First Report dated Dec. 9, 2011 for Application No. AU 2006292818.
Australian Office Action dated Feb. 12, 2014 for Application No. AU 2012202103.
Australian Office Action dated Aug. 1, 2014 for Application No. AU 2012244072.
Australian Office Action dated Sep. 17, 2014 for Application No. AU 2012202103.
Australian Office Action dated Sep. 30, 2014 for Application No. AU 2009293312.
Australian Office Action dated Oct. 1, 2014 for Application No. AU 2009333010.
Australian Office Action dated Jul. 8, 2015 for Application No. AU 2012244072.
Canadian Office Action dated Jul. 10, 2015 for Application No. CA 2,617,054.
Canadian Office Action dated Dec. 16, 2015 for Application No. CA 2,751,665.
Chinese Office Action, First Office Action dated Jan. 29, 2013 for CN 200980152995.1.
Chinese Office Action, First Office Action dated Nov. 5, 2012 for CN 200980137396.1.
Chinese Office Action, Decision of Rejection, dated 2014 for Application No. CN 200980152995.1.
Chinese Office Action, Third Office Action, dated Feb. 27, 2014 for Application No. CN 200980152995.1.
Chinese Office Action and Search Report dated Feb. 10, 2015 for Application No. CN 201310672731.6.
Chinese Search Report dated Jan. 11, 2013 for Application No. CN 200980152995.0.
Chinese Search Report dated Oct. 29, 2012 for Application No. CN 200980137396.1.
European Communication dated Jan. 7, 2013 for Application No. EP 08746715.5.
European Communication dated Apr. 11, 2013 for Application No. EP 05778834.1.
European Communication dated Apr. 19, 2012 for Application No. EP 08746715.5.
European Communication dated May 10, 2013 for Application No. EP 06751637.7.
European Communication dated Jun. 19, 2009 for Application No. EP 05773189.
European Communication dated Aug. 1, 2012 for Application No. EP 06784759.0.
European Communication dated Aug. 24, 2012 for Application No. EP 05798331.4.
European Communication dated Sep. 4, 2008 for Application No. EP 05773189.
European Communication dated Nov. 9, 2012 for Application No. EP 07750248.2.
European Communication dated Sep. 27, 2011 for Application No. EP 06800540.4.
European Communication dated Sep. 3, 2013 for Application No. EP 12182998.0.
European Communication dated Feb. 26, 2014 for Application No. EP 06800540.4.
European Communication dated Aug. 11, 2014 for Application No. EP 12182998.0.
European Communication dated Aug. 26, 2014 for Application No. EP 12183000.4.
European Communication dated Nov. 26, 2014 for Application No. EP 07836108.6.
European Communication dated Feb. 17, 2016 for Application No. EP 12162712.9.
European Exam Report dated Feb. 8, 2007 for Application No. EP 02716734.5.
European Exam Report dated Feb. 22, 2006 for Application No. EP 02716734.5.
European Search Report and Written Opinion dated Sep. 11, 2009 for Application No. EP 06815174.
European Search Report dated Jan. 9, 2013 for Application No. EP 12183000.
European Search Report dated Jan. 11, 2013 for Application No. EP 12183002.
European Search Report dated Mar. 16, 2010 re Application No. EP 06718986.
European Search Report dated Jul. 23, 2012 for Application No. EP 12162709.
European Search Report dated Jul. 24, 2012 for Application No. EP 12162712.
European Search Report dated Aug. 6, 2013 for Application No. EP 13172140.
European Search Report dated Aug. 31, 2012 for Application No. EP 12173295.
European Search Report dated Sep. 9, 2013 for Application No. EP 13179223.
European Search Report dated Sep. 27, 2011 for Application No. EP 10182961.
European Search Report dated Sep. 29, 2011 for Application No. EP 10182893.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated May 19, 2015 for Application No. EP 08746464.0.
European Search Report dated Jun. 23, 2015 for Application No. EP 12162712.9.
European Search Report dated Jun. 23, 2015 for Application No. EP 12162709.5.
Extended European Search Report dated Jan. 27, 2014 for Application No. EP 108426321.1
Extended European Search Report dated Sep. 15, 2015 for Application No. EP 15163549.7.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Sep. 25, 2007 for Application No. PCT/US06/002004.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability and Written Opinion dated Nov. 18, 2008 for Application No. PCT/US07/11449.
International Preliminary Report on Patentability dated Feb. 15, 2008 for Application No. PCT/US05/13617.
International Preliminary Report on Patentability dated Jun. 29, 2011 for Application No. PCT/US2009/069143.
International Preliminary Report on Patentability dated Aug. 7, 2006 for Application No. PCT/US05/25371.
International Search Report and Written Opinion dated Apr. 10, 2006 for Application No. PCT/US05/25371.
International Search Report and Written Opinion dated Jul. 21, 2008 for Application No. PCT/US05/033090.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report and Written Opinion dated Oct. 6, 2010 for Application No. PCT/US2010/040548.

(56) References Cited

OTHER PUBLICATIONS

International Written Opinion dated Aug. 9, 2011 for Application No. PCT/US2011/038751.
International Search Report dated Mar. 31, 2010 for Application No. PCT/US2009/069143.
International Search Report dated May 8, 2007 for Application No. PCT/US2006/16026.
International Search Report dated May 18, 2012 for Application No. PCT/US2011/052321.
International Search Report dated May 29, 2008 for Application No. PCT/US07/021170.
International Search Report dated May 29, 2008 for Application No. PCT/US07/021922.
International Search Report dated Jun. 3, 2002 for Application No. PCT/EP02/01228.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 8, 2010 for Application No. PCT/US2010/027837.
International Search Report dated Jul. 17, 2008 for Application No. PCT/US06/036960.
International Search Report dated Aug. 17, 2007 for Application No. PCT/US05/013617.
International Search Report dated Aug. 25, 2008 for Application No. PCT/US2008/000911.
International Search Report dated Aug. 29, 2007 for Application No. PCT/US06/002004.
International Search Report dated Aug. 9, 2011 for Application No. PCT/US2011/038751.
International Search Report dated Sep. 10, 2008 for Application No. PCT/US07/016212.
International Search Report dated Sep. 25, 2007 for Application No. PCT/US06/037167.
International Search Report dated Oct. 15, 2008 for Application No. PCT/US2008/061048.
International Search Report dated Oct. 19, 2007 for Application No. PCT/US07/003394.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
Japanese Office Action, Examiner's Decision of Refusal dated Oct. 18, 2011 for Application No. JP 2007-509632.
Japanese Office Action, Notification of Reasons for Refusal dated Jan. 24, 2012 for Application No. JP 2007-532485.
Japanese Office Action, Notification of Reasons for Refusal dated Apr. 26, 2011 for Application No. JP 2007-532485.
Japanese Office Action, Notification of Reasons for Refusal dated Jun. 25, 2013 for Application No. JP 2012-131840.
Japanese Office Action, Notification of Reasons for Refusal dated Aug. 16, 2011 for Application No. JP 2008-516013.
Japanese Office Action, Notification of Reasons for Refusal dated Sep. 18, 2013 for Application No. JP 2011-527942.
Japanese Office Action, Notification of Reasons for Refusal dated Nov. 8, 2011 for Application No. JP 2008-524250.
Japanese Office Action, Notification of Reasons for Refusal dated Nov. 12, 2013 for Application No. JP 2011-542562.
Japanese Office Action, Notification of Reasons for Refusal dated Jan. 7, 2014 for Application No. JP 2012-266049.
Japanese Office Action, Reasons for Refusal, dated Sep. 2, 2014 for Application No. JP 2012-544859.
Japanese Office Action, Reasons for Refusal, dated Jun. 9, 2015 for Application No. JP 2014-147174.
Japanese Office Action, Notification of Reasons for Refusal dated 03/2x92/2016 for Application No. JP 2012-266049.
Partial European Search Report dated Mar. 25, 2008 for Application No. EP 07252018.
Partial European Search Report dated Sep. 20, 2007 for Application No. EP 07252018.
Partial International Search Report dated Feb. 7, 2012 for Application No. PCT/US2011/052321.
PCT Search Report dated Nov. 30, 2009 for Application No. UPCT/US2009/057203.
Russian Office Action dated Mar. 19, 2013 for Application No. RU 2011130530.
Russian Office Action dated Sep. 28, 2012 for Application No. RU 2011130530.
Supplemental European Search Report dated Jan. 28, 2011 for Application No. EP 07777004.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Mar. 31, 2011 for Application No. EP 05798331.
Supplemental European Search Report dated Jun. 22, 2010 for Application No. EP 06784759.
Supplemental European Search Report dated Aug. 30, 2011 for Application No. EP 06800540.
Supplemental European Search Report dated Sep. 23, 2010 for Application No. EP 08746715.
Supplemental European Search Report dated Sep. 29, 2011 for Application No. EP 07750248.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search dated Jan. 14, 2014 for Application No. EP 13184009.
Supplemental European Search Report dated Jan. 17, 2014 for Application No. EP 1084263.
Supplemental European Search Report dated Feb. 13, 2014 for Application No. EP 08746464.
Supplemental European Search Report dated Dec. 9, 2014 for Application No. EP 07839152.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.

(56) References Cited

OTHER PUBLICATIONS

USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 14/221,550, filed Mar. 21, 2014.
U.S. Appl. No. 11/789,705, filed Apr. 24, 2007.
U.S. Appl. No. 11/804,308, filed May 16, 2007.
U.S. Appl. No. 11/804,309, filed May 16, 2007.
U.S. Appl. No. 14/221,621, filed Mar. 21, 2014.
U.S. Appl. No. 14/221,714, filed Mar. 21, 2014.
U.S. Appl. No. 14/265,888, filed Apr. 30, 2014.
U.S. Appl. No. 14/266,002, filed Apr. 30, 2014.
U.S. Appl. No. 14/266,025 filed Apr. 30, 2014.
U.S. Appl. No. 14/327,593, filed Jul. 10, 2014.
U.S. Appl. No. 14/464,948, filed Aug. 21, 2014.
U.S. Appl. No. 14/993,444, filed Jan. 12, 2016.
U.S. Appl. No. 15/083,826, filed Mar. 29, 2016.
U.S. Appl. No. 15/417,655.
U.S. Appl. No. 15/417,712.
U.S. Appl. No. 15/443,319.
U.S. Appl. No. 15/465,978.
U.S. Appl. No. 15/595,319.
U.S. Appl. No. 15/624,093.
U.S. Appl. No. 15/624,111.
U.S. Appl. No. 15/651,101.
U.S. Appl. No. 15/795,834.
U.S. Appl. No. 16/106,653.
U.S. Appl. No. 16/156,112.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/929,808.
U.S. Appl. No. 12/143,698.
Dictionary.reference.com/browse/bent; Definition of "bent" as accessed on Sep. 10, 2015.
"Durometer Made Easy Durometer Hardness Scales—General Reference Guide." Paramount Industries, Inc. 2008. Accessed online: http://www.paramountind.com/pdfs/paramount_durometer_scale_guide.pdf.
"Durometer Shore Hardness Scale." Smooth-On, Inc. 2016. Accessed online: https://www.smooth-on.com/page/durometer-shore-hardness-scale/.
Merriam-Webster definition of "lumen" as accessed Jun. 10, 2016, http://www.merriam-webster.com/dictionary/lumen.
Nasal Surgery and Accessories, Jan. 25, 2007; www.technologyforlife.com.au/ent/nasal.html.
Canadian Office Action dated Jun. 20, 2016 for Application No. CA 2,617,054.
European Communication dated Sep. 26, 2016 for Application No. EP 12162712.9.
European Communication dated May 12, 2012 for Application No. EP 09792627.3.
European Communication dated Jul. 14, 2017 for Application No. EP 06784759.0.
European Communication dated Aug. 2, 2017 for Application No. EP 12173295.2.
European Search Report dated Jan. 27, 2014 for Application No. EP 13184009.2.
European Search Report dated Jun. 28, 2017 for Application No. EP 17159646.3.
Supplemental European Search Report dated Mar. 24, 2010 for Application No. EP 07836108.6.
Supplemental European Search Report dated Sep. 8, 2011 for Application No. EP 06800540.4.
Supplemental European Search Report dated Feb. 27, 2014 for Application No. EP 08746464.0.
Supplemental European Search Report dated Dec. 17, 2014 for Application No. EP 07839152.1.

\* cited by examiner

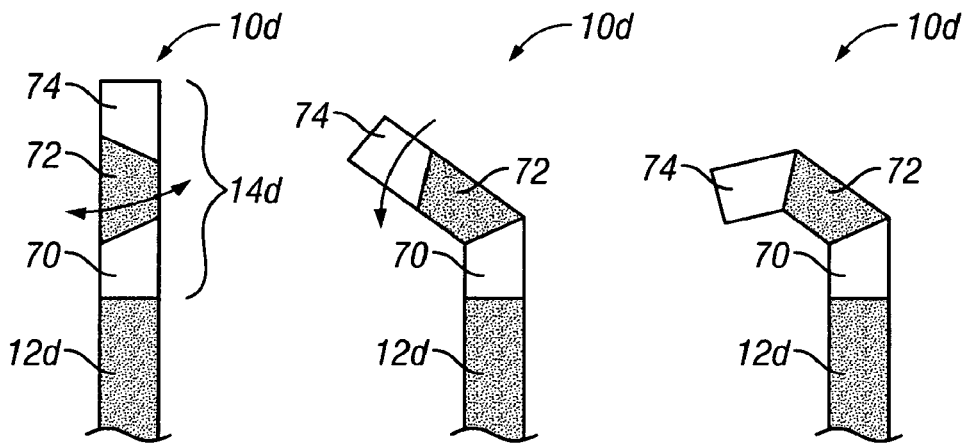
FIG. 4A    FIG. 4B    FIG. 4C
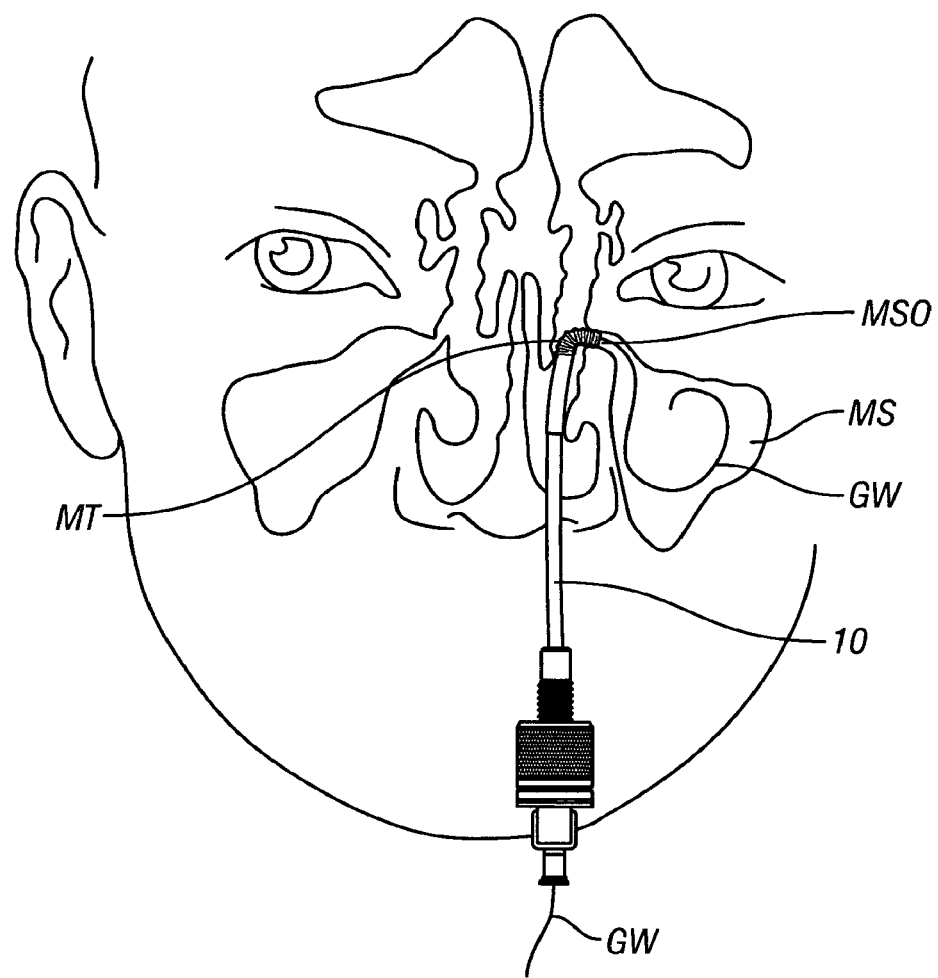
FIG. 5

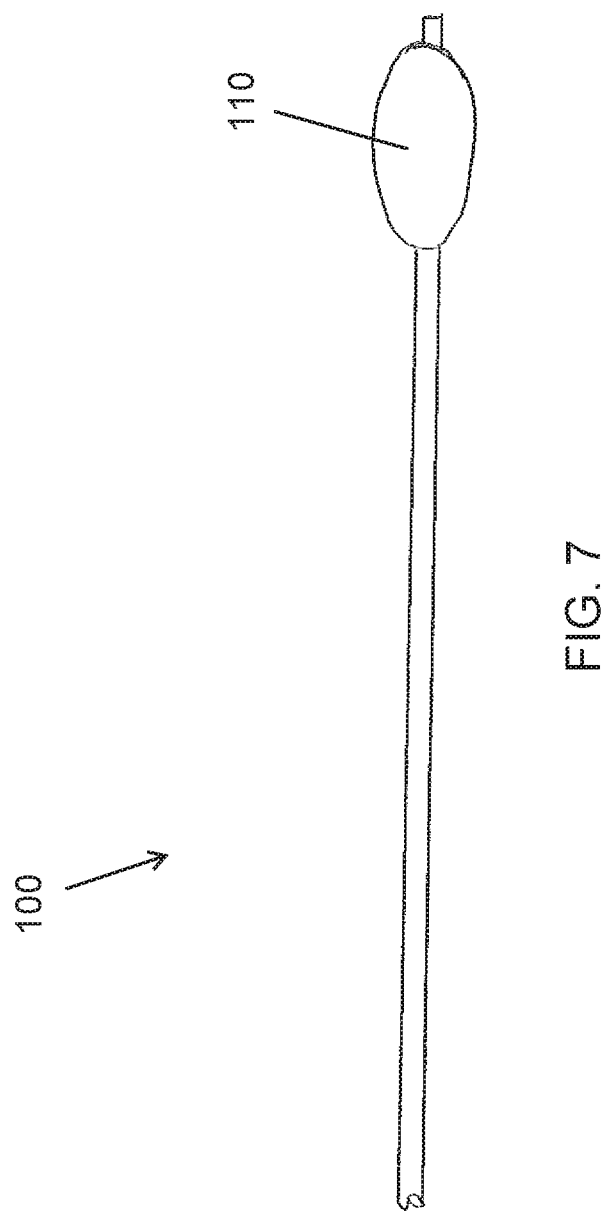

DEFLECTABLE GUIDE CATHETERS AND RELATED METHODS

RELATED APPLICATIONS

This application is a continuation of U.S. patent application Ser. No. 11/804,308, entitled Deflectable guide catheters and related methods," filed on May 16, 2007, issued as U.S. Pat. No. 10,188,413 on Jan. 29, 2019, which is a continuation in part of the following copending United States patent applications: (1) Ser. No. 11/037,548 filed Jan. 18, 2005, issued as U.S. Pat. No. 7,462,175 on Dec. 9, 2008, which is a continuation in part of Ser. No. 10/829,917 filed Apr. 21, 2004, issued as U.S. Pat. No. 7,654,997 on Feb. 2, 2010; (2) Ser. No. 11/150,847 filed Jun. 10, 2005, issued as U.S. Pat. No. 7,803,150 on Sep. 28, 2010, which is a continuation in part of Ser. No. 10/944,270 filed Sep. 17, 2004, published as U.S. Pub. No. 2006/0004323 on Jan. 5, 2006, now abandoned, which is a continuation in part of Ser. No. 10/829,917 filed Apr. 21, 2004, issued as U.S. Pat. No. 7,654,997 on Feb. 2, 2010; (3) Ser. No. 11/193,020 filed Jul. 29, 2005, published as U.S. Pub. No. 2006/0063973 on Mar. 23, 2006, now abandoned, which is a continuation in part of Ser. No. 10/944,270 filed Sep. 17, 2004, published as U.S. Pub. No. 2006/0004323 on Jan. 5, 2006, now abandoned, which is a continuation in part of Ser. No. 10/829,917 filed Apr. 21, 2004, issued as U.S. Pat. No. 7,654,997 on Feb. 2, 2010; and (4) Ser. No. 11/436,892 filed May 17, 2006, published as U.S. Pub. No. 2007/0208252 on Sep. 6, 2004, now abandoned, which is a continuation in part of (a) Ser. No. 11/116,118 filed Apr. 26, 2005, issued as U.S. Pat. No. 7,720,521 on May 18, 2010, which is a continuation in part of Ser. No. 10/829,917 filed Apr. 21, 2004, issued as U.S. Pat. No. 7,654,997 on Feb. 2, 2010, (b) Ser. No. 10/912,578 filed Aug. 4, 2004, issued as U.S. Pat. No. 7,361,168 on Apr. 22, 2008, (c) Ser. No. 10/944,270 filed Sep. 17, 2004, published as U.S. Pub. No. 2006/0004323 on Jan. 5, 2006, now abandoned, and (d) Ser. No. 11/037,548 filed Jan. 18, 2005, issued as U.S. Pat. No. 7,462,175 on Dec. 9, 2008, the entire disclosure of each such application (except U.S. patent application Ser. No. 11/804,308) being expressly incorporated herein by reference.

FIELD OF THE INVENTION

The present invention relates generally to medical apparatus and methods and more particularly to deflectable guide catheters and their methods of manufacture and use.

BACKGROUND OF THE INVENTION

U.S. Pat. No. 5,562,619 (Mirarchi, et al.) describes a deflectable catheter that may be inserted percutaneously and advanced through the vasculature to access the heart or brain. An elongated wound wire coil extends through a hollow catheter body, such coil being constructed and arranged to enable the catheter body to withstand reactive compressive load without distortion during application of tension on the pull wire and to transmit torque from the proximal to the distal tip portion of the catheter to enhance fidelity of rotational positioning of the distal tip in response to rotational orientation of the proximal portion of the catheter. The coil is in frictional torque-transmitting relationship with the interior of the hollow shaft substantially along the common length of the catheter body when the catheter is bent. This deflectable catheter purportedly has augmented throw for one-handed operation.

U.S. Pat. No. 6,755,812 (Peterson et al.) describes a deflectable, telescoping guide catheter having an inner guide with a pre-formed distal tip, an outer guide with a predetermined deflection location, and a proximal actuator. The inner guide can be longitudinally extended and axially rotated relative to the outer guide. The proximal actuator can adjustably change a bend angle of the predetermined deflection location. The catheter can be deployed with the inner guide retracted inside the distal end of the outer catheter. The extensible and rotatable inner catheter can be combined with the adjustable bend angle of the outer guide to provide an improved system for accessing and cannulation of venous structures.

U.S. Pat. No. 5,195,168 (Lundquist, et al.) describes a steering mechanism for use in a variety of medical catheters. Such steering mechanism includes a steering shaft coupled to a controller which manipulates the distal end of the steering shaft. The steering shaft includes a flexible coiled spring having a lead spring fixed in position with respect to a distal end thereof in the distal end of the steering shaft. The distal ends of one or more steering wires is/are affixed to the lead spring. The steering wires extend through the steering shaft to the controller, and the steering apparatus of the controller is used to place tension on the steering wire(s). The attachment of the distal ends of the steering wires to the lead spring may be opposite one another or may be offset for providing greater maneuverability. Tension may be placed on the steering wires by wedges mounted transversely to the controller housing, or by rotation of a shaft mounted transversely to the controller housing, the steering wires being attached to the shaft such that rotation in one direction tenses one steering sire, and rotation in the other direction tenses the other steering wire. Two independently rotatable shafts may be used to separately control the two steering wires. The steering shaft is adapted for insertion into a lumen of a catheter for use in guiding the distal end of the catheter to a treatment site within a patient. The steering mechanism may also be used in conjunction with tools or apparatus which must reach into difficult locations, such as engines or other machines.

U.S. Pat. No. 5,733,248 (Adams et al.) describes a universal guide catheter that has a shaping mandrel inserted into a lumen of the catheter. The shaping mandrel changes from a first configuration to a second configuration after the catheter has been inserted into the body. In some embodiments the shaping mandrel is formed of a shape memory material which changes from the first shape to the second shape as the catheter warms to body temperature.

U.S. Pat. No. 6,585,717 (Wittenberger et al.) describes a deflection mechanism for a medical device comprising a plurality of rings and a connecting structure connecting the plurality of rings. This deflection mechanism is purportedly that are positionable in a catheter or other flexible body to cause a distal portion of the catheter or other flexible body to deflect or curve in more than one direction in a single plane and/or in more than one plane and/or to be deflected more than 360 degrees to form a loop.

U.S. Pat. No. 6,890,329 (Carroll et al.) describes another deflection mechanism that is purportedly capable of deflecting portions of a catheter or other flexible body in more than one direction in a single plane and/or in more than one plane and/or in a curve of more than 360 degrees to form a loop.

Also, Mols, B., *Moveable Tool Tip for Keyhole Surgery*, Delft Outlook, Vol. 3, Pages 13-17 (2005), describes a moveable tip which incorporates a spring and one or more pull cables to facilitate deflection or steering of the tip of the device before or after insertion into a patient's body during keyhole (e.g., laparoscopic) surgery.

Additionally, Piers et al., *A Flexible Distal Tip With Two Degrees of Freedom for Enhanced Dexterity in Endoscopic Robot Surgery*, Proceedings 13th Micromechanics Europe Workshop, Pages 271-74 (2002) describes a flexible tube that can be bent by pulling cables running along its length. An outer tube formed on NiTi alloy is disposed on a distal portion of the flexible tube and is cut into a series of rings connected by thin elastic joints.

Also, a number of deflectable guide catheters are on sale and in public use, including for example, the Morph™ Vascular Access Catheter (BioCardia, South San Francisco, Calif.) which is intended to serve as a conduit for access in the coronary vasculature and chambers of the heart and the Attain® Deflectable Catheter Delivery System (Medtronic, Inc., Minneapolis, Minn.) which is intended for use in coronary sinus cannulation and delivery of electronic pacing leads.

Recently, a transnasal, catheter-based procedure has been developed for treating sinusitus and other disorders of the ear, nose throat and paranasal sinuses (Balloon Sinuplasty™ Procedure; Acclarent, Inc., Menlo Park, Calif.). In this procedure, an appropriately shaped guide catheter having a fixed distal curve is selected from a series of available guide catheter shapes, and the selected guide catheter is advanced though a nostril to a position where the distal end of the guide catheter is adjacent to the ostium of a paranasal sinus. A guidewire is ten advanced through the guide catheter and into the paranasal sinus. Thereafter, a balloon catheter is advanced over the guidewire and through the guide catheter, to a position where the balloon is within the ostium of the paranasal sinus. The balloon is then inflated causing enlargement and restructuring of the ostium, thereby improving sinus drainage. At present, the sinus guide catheters are commercially available in a variety of fixed shapes having distal curves from 0 degrees to 110 degrees (Relieva® Sinus Guide Catheters, Acclarent, Inc., Menlo Park, Calif.). The surgeon typically selects a sinus guide catheter which has a fixed distal curve that is believed to be best for accessing a particular sinus ostium. The fixed distal; curvature of the selected sinus guise catheter cannot be changed while the guide catheter is inserted in the subject's nose.

U.S. patent application Ser. No. 11/037,548, issued as U.S. Pat. No. 7,462,175 on Dec. 9, 2008; Ser. No. 11/150,847, issued as U.S. Pat. No. 7,803,150 on Sep. 28, 2010; Ser. No. 11/193,020, published as U.S. Pub. No. 2006/0063973, now abandoned; and Ser. No. 11/436,892, published as U.S. Pub. No. 2007/0208252 on Sep. 6, 2004, now abandoned, of which this application is a continuation in part, describe the use of deflectable or steerable guide catheters in the performance of the Balloon Sinuplasty™ procedure as well as various other procedures wherein deflectable or steerable guide catheters are used to guide devices (e.g., guidewires, catheters, implantable drug delivery devices, etc.) to desired locations within the ear, nose, throat or cranium.

There remains a need for further development of new deflectable guide catheters having variable shapes and their methods of manufacture and use for transnasal and/or other applications.

SUMMARY OF THE INVENTION

In accordance with the present invention, there is provided a method for delivering a substance or device (e.g., a guidewire, catheter, implant or any other diagnostic or therapeutic device) to a desired location within the ear, nose, throat or cranium of a human or animal subject using a deflectable guide catheter that has an elongate catheter shaft, a distal portion of the shaft which is deflectable, a distal end and a deflection control that remains outside of the subject's body and is useable to cause the distal portion of the shaft to deflect form a first configuration to a second configuration. Such method generally includes the steps of (A) inserting the guide catheter, distal end first, through a nostril of the subject, (B) using the deflection control to deflect the distal portion of the catheter shaft from the first configuration to the second configuration, (C) positioning the distal end at or near the desired location; and (D) advancing a device or delivering a substance or flow of energy through the guide catheter and to or through the desired location.

Further in accordance with the present invention, there are provided deflectable guide catheter devices that are useable to perform the above summarized method as well as other methods wherein it is desired to deliver a substance or device (e.g., a guidewire, catheter, implant or any other diagnostic or therapeutic device) to a desired location anywhere within the body of a human or animal subject. In general, these guide catheter devices of the present invention comprise (A) a substantially rigid tube (e.g., a metal hypotube) having a lumen, an inner surface, an outer surface and a distal end, (B) a deflectable member (e.g., a spring member) having a distal end, said helical spring member being attached to and extending from the distal end of the substantially rigid tube, (C) a tubular plastic inner jacket having an inner surface, an outer surface and a lumen, said inner jacket extending through the lumen of the metal outer tube and through the helical spring member; (D) an outer jacket (e.g., a separate tube, sheath or coating) substantially covering at least the deflectable member and (E) a deflector member extending between the inner surface of the substantially rigid tube and the outer surface of the tubular inner jacket, said deflector member being attached to the helical spring member at or near its distal end such that, when the deflector member is pushed or pulled, a distal portion of the guide catheter will deflect. In embodiments intended for delivering devices or substances transnasally to locations within the ear, nose, throat or cranium of a human or animal subject, the deflectable guide catheter device may have a length of less than approximately 25 cm and in some embodiments less than 15 cm.

Still further in accordance with the present invention, there are provided other deflectable guide catheter devices and methods of use. These other deflectable guide catheter devices generally comprise a tubular catheter shaft that includes a proximal segment having a beveled distal end and a distal segment having a beveled proximal end that abuts against the beveled distal end of the proximal segment. The distal segment is rotatable between a) a first position where the beveled proximal end of the distal segment abuts with the beveled distal end of the proximal segment in a manner that causes the catheter shaft to be substantially straight and b) a second position wherein the beveled proximal end of the distal segment abuts with the beveled distal end of the proximal segment in a manner that causes the catheter shaft to be curved. Also, in some embodiments, such deflectable guide catheter device may further include a medial segment disposed between the proximal and distal segments. Such medial segment has a beveled proximal end and a beveled distal end. The beveled proximal end of the medial segment abuts against the beveled distal end of the proximal segment and the beveled distal end of the medial segment abuts against the beveled proximal end of the distal segment. In this embodiment, the medial and distal segments are independently rotatable to impart different curvatures to the catheter shaft. In operation, the medial and/or distal segments are rotated to provide a desired curvature of the catheter shaft prior to or after insertion of the catheter shaft into the body of a human or animal subject.

Further aspects, elements and advantages of the present invention will be understood by those of skill in the art upon reading of the detailed description set forth herebelow.

BRIEF DESCRIPTION OF THE DRAWINGS

FIGS. 4A through 4C are partial, schematic diagrams of the distal end of another embodiment of a deflectable guide catheter of the present invention in different states of deflection.

FIG. 5 is an anatomical diagram of the head of a human subject showing certain paranasal anatomical structures, a deflectable guide catheter of the present invention positioned adjacent to the ostium of the left maxillary sinus and a guidewire advanced through the guide catheter and into the left maxillary sinus.

FIG. 7 shows a dilator including a balloon.

DETAILED DESCRIPTION

The following detailed description and the accompanying drawings are intended to describe some, but not necessarily all, examples or embodiments of the invention. The contents of this detailed description and the accompanying drawings do not limit the scope of the invention in any way.

Figure 1:
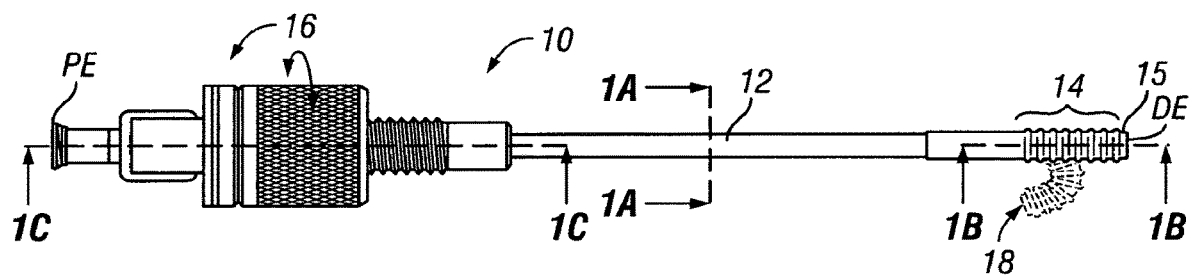
FIG. 1 is a side view of one embodiment of a deflectable guide catheter device of the present invention.
Figure 1A:
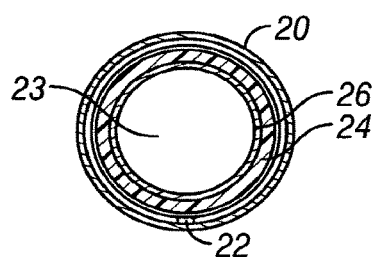
FIG. 1A is a transverse sectional view through line 1A-1A of FIG. 1.
Figure 1B:
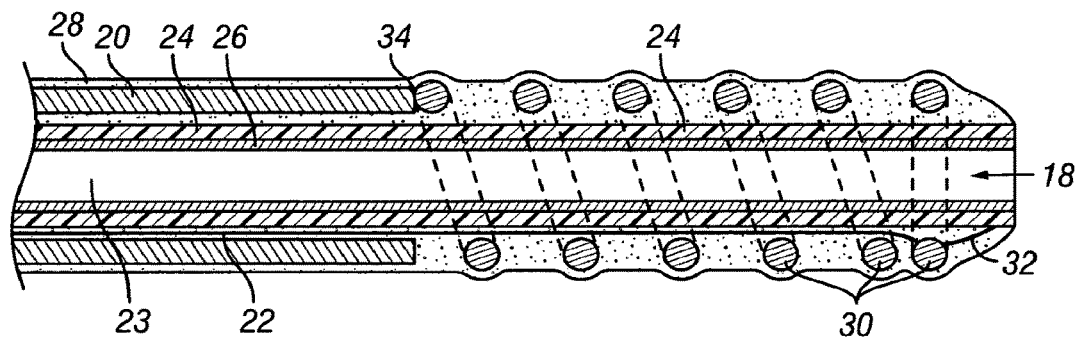
FIG. 1B is a partial longitudinal sectional view through line 1B-1B of FIG. 1.
Figure 1C:
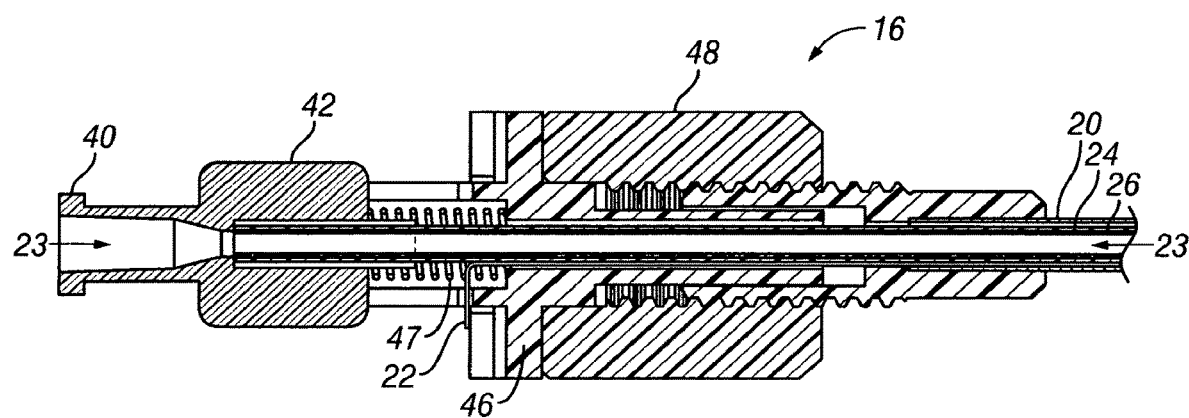
FIG. 1C is a partial longitudinal sectional view through line 1C-1C of FIG. 1.

FIGS. 1 through 1C show one embodiment of a deflectable transnasal guide catheter device 10 of the present invention. In this embodiment, the guide catheter device 10 generally comprises an elongate catheter shaft 12 having a lumen 23, a deflectable distal portion 14 adjacent to is distal end DE and a proximal assembly 16 on its proximal end PE. As seen in FIGS. 1A and 1B, the catheter shaft 12 may be constructed of a substantially rigid tube 20, a deflector member which in this example is a helical spring member 30, a tubular inner jacket 24, an outer jacket 28 and, in some embodiments, an optional inner liner 26. In some embodiments, an energy guide such as a fiberoptic laser guide or wire for delivering current may extend through or replace the lumen 23.

The substantially rigid tube 20 has a lumen, an inner surface, an outer surface and a distal end and may be formed of malleable material including metals such as stainless steel hypotube. In the particular transnasal 30 embodiment shown, this substantially rigid tube 20 may be formed of hypotube having an outer diameter of about 2 mm to about 4 mm. The helical spring member 30 may be connected to the distal end of the substantially rigid tube 20 by solder, adhesive, a weldment or any other appropriate attachment member or substance 34, as seen in FIG. 1B. The helical spring member may alternatively comprise a section of the substantially rigid tube 20 in which a helical cut or one or more other cut(s), groves, openings, or weakened area(s) is/are formed. In some embodiments, the helical spring member may be formed of metal wire having a diameter of from about 0.016 inch to about 0.017 helically wound to a pitch of from about 0.060 inch to about 0.100 inch. In catheters sized for transnasal use, such helical spring member may also have a length of from about 0.625 inch to about 0.75 inch and an outer diameter of from about 0.100 inch to about 0.156 inch. The tubular inner jacket 24 has an inner surface, an outer surface and a lumen. This tubular inner jacket 24 may be formed of any suitable elastomer or other material, such as polyurethane, and may comprise a separate tube that is mounted on or fused in place or a coating or layer or material that has been applied by a suitable procedure such as dip coating, vapor deposition, painting, etc. In the particular non-limiting example shown in FIG. 1B, the tubular inner jacket 24 extends through the lumen of the substantially rigid tube 20 and, through the helical spring member 30, protruding slightly beyond the distal end of the spring member 30. A pull member 22, such as metal wire, monofilament or other suitable material, extends between the inner surface of the substantially rigid tube 20 and the outer surface of the tubular inner jacket 24. Such pull member 22 further extends through the spring member 30 and is connected to the distal end of the spring member 30 by solder, adhesive, weldment or any other appropriate attachment member or substance 34 and/or by tying, looping or twining the pull member around the wire, strand or other member of which the helical spring member 30 is formed. An outer jacket 28, such as an elastomeric (e.g., polyurethane) tube, may be disposed over the outer surface of the spring member 30 and, optionally, may extend in the distal direction to cover some or all of the outer surface of the substantially rigid tubular member 20. In the particular non-limiting example shown in FIGS. 1-1C, the outer jacket 28 extends proximally over the distal 3 cm to 5 cm of the substantially rigid tubular member 20. This outer jacket 28 may comprise a tube that is heat shrunk or otherwise caused to fight snuggly on the distal portion of the device 10. Alternatively, this outer jacket 28 may comprise be fused (e.g., heat fused), adhered by adhesive, solvent welded or otherwise affixed (e.g., sewn, stitched, etc.) to at least a portion of the inner jacket 24. For example, during manufacture, a mandrel may be inserted into the distal end of the device lumen 23 and heat may be applied to cause the outer jacket to heat shrink and to fuse at least its distal end to at least the distal end of the inner jacket 24. In some cases, the heating process may cause the inner jacket 24 and outer jacket 28 to melt or fuse together over the length of the spring member 30, substantially filling the helical space within the spring member 30 with elastomeric material as seen in FIG. 1B. Alternatively, as explained above, the outer jacket 28 may comprise a layer of material (e.g., polymeric coating material) that has been applied by a suitable process such as dip coating, vapor deposition, painting, etc. to form the outer jacket 28, as shown.

Optionally, in some embodiments, a tubular inner liner 26 such as a thin walled polytetrafluoroethylene (PTFE) tube may extend through all or part of the lumen 23 of the device. Such inner liner 26 (if present) may or may not be fused (e.g., heat fused), adhered by adhesive, solvent welded or otherwise affixed to all or part of the inner jacket 24.

In operation, when the pull member 22 is pulled in the proximal direction, the curvature of the spring member 30 (and the curvature of the deflectable distal portion 14) will increase. Conversely, when the pull member is advanced in the distal direction, the curvature of the spring member 30 (and the curvature of the deflectable distal portion 14) will decrease. In embodiments intended for transnasal insertion and use in accessing the ostia or paranasal sinuses, it is desirable for the distal portion 14 to be deflectable to form curves ranging from about 0 degrees (i.e., substantially straight) to at least about 110 degrees. As will be explained in more detail herebelow, the deflection of the distal portion 14 may be carried out before and/or after the distal portion has been inserted into the body of a human or animal subject.

In some embodiments, the proximal and distal movement of the pull member 22 may be controlled by a deflection control that is located on a portion of the guide catheter device 10 that remains outside of the subject's body. In the particular embodiment of the guide catheter device 10 shown in FIGS. 1-1C, this deflection control comprises a control knob 48 located on the proximal assembly 16. As seen in detail in FIG. 1C, this proximal assembly 16 comprises an externally threaded two-piece body member 46 having a female Luer fitting 40 at its proximal end, the control knob 48 having internal threads that are mated with the external threads of the inner body member 46. Spring 47 applies tension on Luer fitting 40 and liner 26 with respect to body member 46. Pull member 22 is connected to a washer that is in contact with body member 46. When the control knob 48 is rotated in one direction (e.g., clockwise), it advances in the distal direction causing the body member 46 and the pull member 22 to also advance in the distal direction and resulting in a decrease of the curvature of the deflectable distal portion 14. When the control knob 48 is rotated in the opposite direction (e.g., counterclockwise), it retracts in the proximal direction causing the body member 46 and the pull member 22 to also retract in the proximal direction and resulting in an increase in the curvature of the deflectable distal portion 14.

Also, in some embodiments, indicia (e.g., markings, graduations, zones, projections, other visible or tactilely discernable indicators) may be associated with the deflection control to indicate to the operator the present direction and/or degree of curvature of the deflectable distal portion 14. Such indicia may be located on a portion of the device that remains outside of the subject's body to enable the operator to determine the direction or plane in which the deflectable distal portion 14 will curve and/or the degree to which it is presently curved, even though the deflectable distal portion 14 may be located within the subject's body and out of the operator's sight. In the particular embodiment of the guide catheter device 10 shown in FIGS. 1-1C, diametrically opposed wings 42 may extend radially from the proximal assembly 16 in a plane that is the same as or parallel to a plane in which the deflectable distal portion 14 curves, thereby acting as indicia of the direction or plane in which the deflectable distal portion 14 will curve. Also, graduation markings (not shown) may be formed on the proximal assembly 16 to indicate how far the control knob 48 is advanced in the distal direction and the corresponding degree of curvature of the distal portion 14 (e.g., in some embodiments markings may be formed at increments between 0 degrees and approximately 110 degrees, etc.).

Figure 1D:
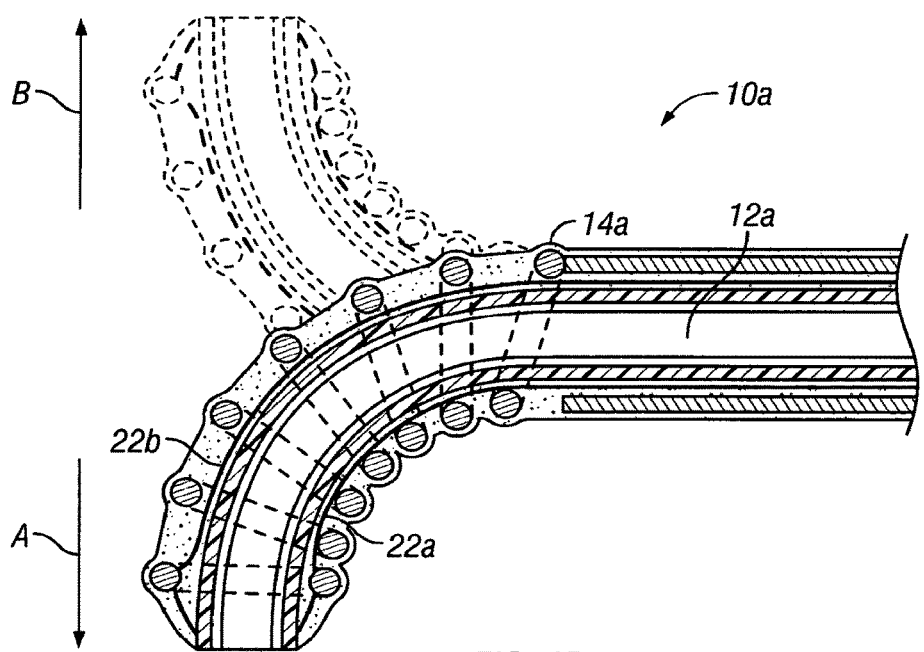
FIG. 1D is a schematic diagram of the distal end of another embodiment of a deflectable guide catheter of the present invention wherein the guide catheter is equipped with more than one pull member so that it may be deflected in more than one direction.

FIG. 1D shows an embodiment of a guide catheter device 10a of the present invention that is essentially the same as that shown in FIGS. 1A-1C, but which includes two pull members 22a, 22b (and may have two deflection controls) to cause the deflectable distal portion 14a of the catheter shaft 12a to deflect in two directions, as shown. It will be appreciated that any of the deflectable guide catheters of the present invention may have a single pull member 22 such that they may be deflectable in a single direction or they may have a plurality of pull members 22a, 22b such that they may alternately be deflected in different directions.

Figure 2:
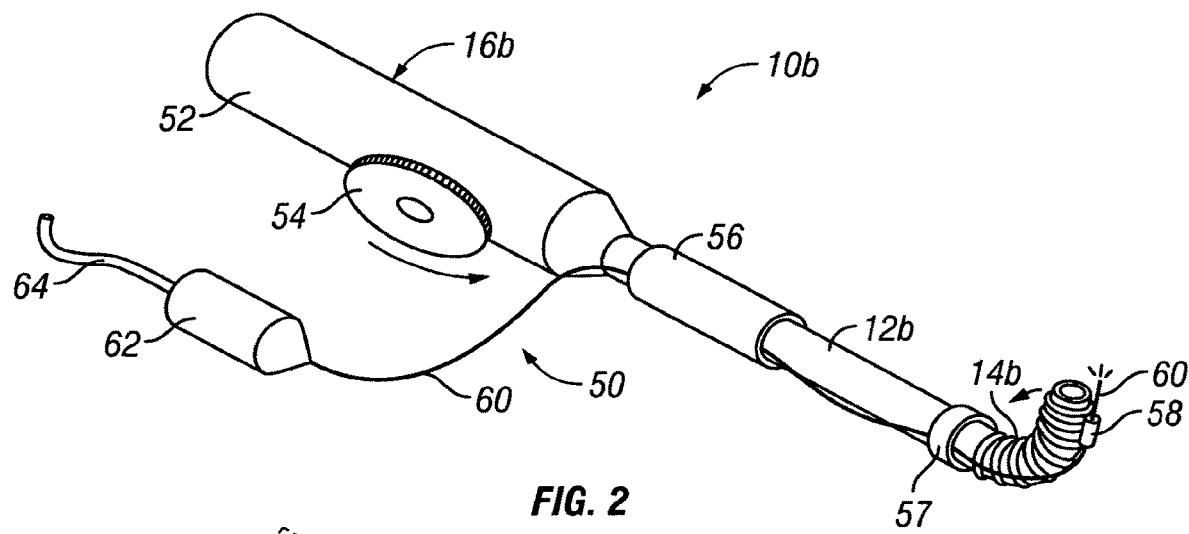
FIG. 2 is a perspective view of another embodiment of a deflectable 20 guide catheter of the present invention in combination with an endoscope system that that may be attached to and used in conjunction with any of the deflectable guide catheters of this invention.

FIG. 2 shows another embodiment of a guide catheter 10b of the present invention that is essentially the same as that shown in FIGS. 1-1C, but wherein the proximal assembly 16b comprises a handpiece body 52 and wherein the deflection control comprises a rotatable wheel 54 mounted on the handpiece 52. Rotatable wheel 54 is linked to the pull member (not seen in FIG. 2) such that when the wheel 54 is rotated in one direction (e.g., clockwise), it will cause the pull member 22 to advance in the distal direction resulting in a decrease of the curvature of the deflectable distal portion 14b of shaft 12b. When the wheel 54 is rotated in the opposite direction (e.g., counterclockwise), it causes the pull member 22 to retract in the proximal direction thereby resulting in an increase in the curvature of the deflectable distal portion 14b of shaft 12b.

Also, the showing of FIG. 2 includes an optional endoscope system 50 that may be attached to or integrated with any deflectable guide catheter of this invention such that the guide catheter device may be used in conjunction with an endoscope system 50. This endoscope system 50 comprises a flexible endoscope 60, such as a fiberoptic scope, that is attached to the shaft 12b of the guide catheter device 10b by way of connectors 56, 57, 58 such as clips, bands, snap-in grooves, etc. In some embodiments, the connectors 56, 57, 58 may be constructed to allow the endoscope 60 to be longitudinally advanced and retracted relative to the shaft 12b of the guide catheter 10b. The endoscope 60 is connected to a camera 62 and the camera 62 is connectable by way of camera cable 64 to a monitor on which an image received through the endoscope 60 may be displayed. Each endoscope 60 has a particular field of view. In this system, the vantage point of the endoscope 60 may be moved by varying the degree of deflection of the deflectable distal portion 14b of the shaft 12b, thus bringing different anatomical structures and/or anatomical areas within the endoscope's field of view. Also, in embodiments where the endoscope 60 is advanceable, the degree of curvature of the deflectable distal portion 14b may be changed to guide the advancement of the endoscope as desired. For example, if it is desired to cause the endoscope to advance through the ostium of a paranasal sinus and into the sinus cavity, the operator may position the distal end DE of the guide catheter 10b near the ostium, visualize the ostium with the scope, and then alter the curvature of the deflectable distal portion 14b as the endoscope 60 is advanced, thereby guiding the endoscope 60 into the ostium as desired. Also, in some applications, such as when it is desired to pass a guidewire or other device through the frontal outflow tract and into a frontal sinus, the operator may be faced with confusing anatomy, such as the presence of one or more false or blind openings in addition to the actual opening through which the guidewire or device is intended to pass. In such instances, the optional endoscope 60 may be used to assist the operator in serially or systematically probing or identifying each available opening, thereby facilitating identification of the correct opening and simplifying passage of the guidewire or device into the correct passage. Examples of endoscopes that may be used in this system include those described in U.S. patent application Ser. No. 11/803,695 entitled "Endoscopic Methods And Devices For Transnasal Procedures" filed May 14, 30 2007, issued as U.S. Pat. No. 9,554,691 on Jan. 31, 2017; Ser. No. 11/647,530, entitled Endoscopic Methods and Devices for Transnasal Procedures filed Dec. 27, 2006, published as U.S. Pub. No. 2007/0167682 on Jun. 19, 2007, now abandoned; Ser. No. 11/725,151 entitled Endoscopic Methods and Devices for Transnasal Procedures filed Mar. 15, 2007, issued as U.S. Pat. No. 9,089,258 on Jun. 28, 2015, and U.S. Provisional Patent Application No. 60/844,874 entitled Endoscopic Methods and Devices for Transnasal Procedures filed Sep. 15, 2006, the entire disclosures of such patent applications being expressly incorporated herein by reference.

Figure 3:
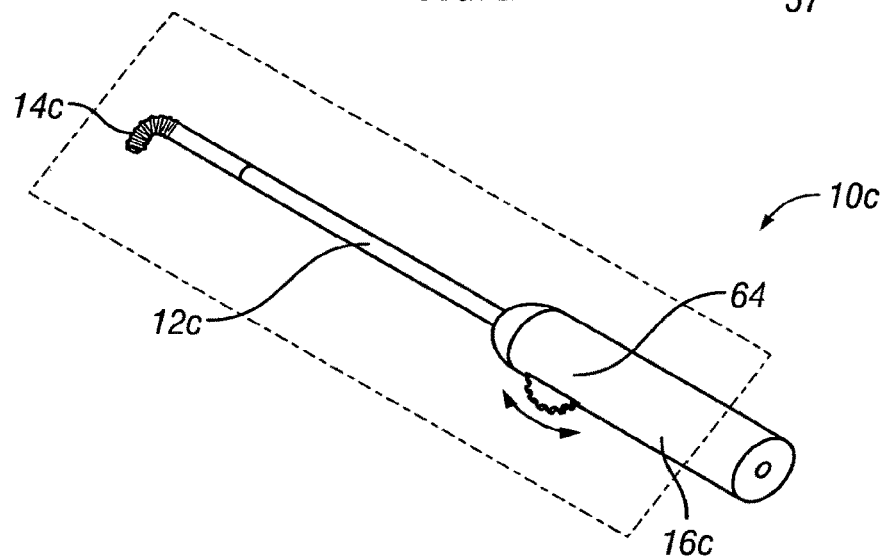
FIG. 3 is a perspective view of another embodiment of a deflectable guide catheter of the present invention.
Figure 3A:
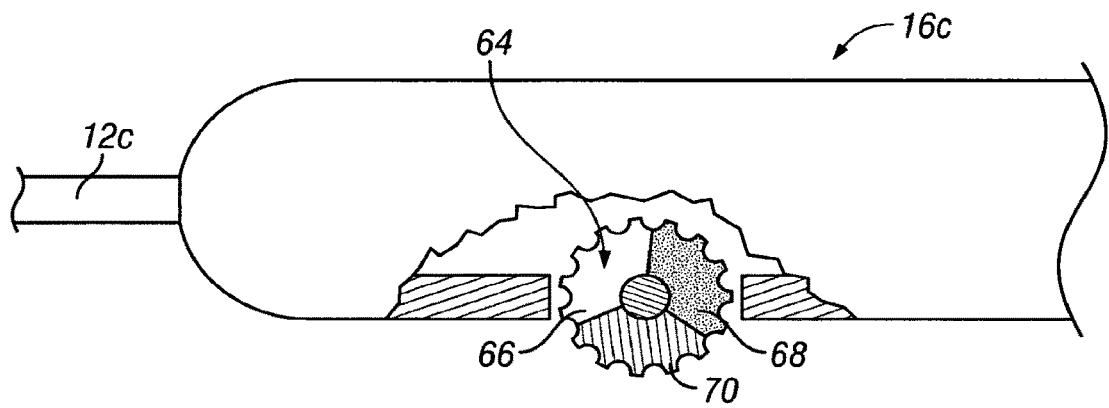
FIG. 3A is a partial, cut-away view of the proximal assembly of the deflectable guide catheter of FIG. 3.

FIGS. 3 and 3A show an embodiment of a deflectable guide catheter 10c which is essentially the same as that shown in FIGS. 1-1C, except that the proximal assembly 16c comprises a handpiece body having a rotatable thumb wheel 64 that rotates about an axis that is perpendicular to the longitudinal axis of the catheter shaft 12c. This rotatable thumb wheel 64 is linked to the pull member (not seen in FIG. 3) such that when the thumb wheel 64 is rotated in one direction (e.g., forward), it will cause the pull member 22 to advance in the distal direction resulting in a decrease of the curvature of the deflectable distal portion 14c of shaft 12c. When the thumb wheel 64 is rotated in the opposite direction (e.g., back), it causes the pull member 22 to retract in the proximal direction thereby resulting in an increase in the curvature of the deflectable distal portion 14c of shaft 12c. As seen in FIG. 3, the thumb wheel 64 may extend in a plane and/or direction that is the same or parallel to the plane and/or direction in which the deflectable distal portion 14c will curve, thereby acting as indicia of the direction and/or plane of curvature. Additionally, as seen in the cut away view of FIG. 3A, indicia of the degree to which the deflectable distal portion 14c is presently curved may be provided on the thumb wheel 64. For example, three colored zones 66, 68, 70 may be formed on the thumb wheel 64. A first (e.g., white) zone 66 may be visible and aligned with a mark on the handpiece when the deflectable portion 14c is curved from about 0 degrees (i.e., substantially straight) to about 36.6 degrees, a second (e.g., red) zone 68 may be visible and aligned with a mark on the handpiece when the deflectable portion 14c is curved from about 36.7 to about 73.2 degrees and third (e.g., blue) zone 70 may be visible and aligned with a mark on the handpiece when the deflectable portion 14c is curved from about 73.3 degrees to about 110 degrees. It is to be appreciated that may other types of indicia (e.g., hash marks or graduations by degree) may be employed as an alternative to the colored zones 66, 68, 70 shown in FIG. 3A.

As those of skill in the art will appreciate, deflection mechanisms known in the art, other than those described in these examples, may alternatively be used in any of the deflectable catheters of this invention, including but not limited to: slides, triggers, hydraulics, electromagnetic field activation, shape memory materials which respond to current or temperature change, a straight stylet that is insertable into a catheter that is biased to a curved configuration to overcome a curve bias thereby straightening the catheter, a curved stylet that that is insertable into a catheter that is biased to a straight configuration to cause the catheter to assume a curved shape, etc.

FIGS. 4A through 4C show another embodiment of a deflectable guide catheter 10d which may be substantially the same as that shown in FIGS. 1-1C, but wherein the deflectable portion 14d of shaft 12d includes a proximal segment 70 having a beveled distal end, a rotatable medial segment having beveled proximal and distal ends and a rotatable distal segment 74 having a beveled proximal end. The beveled proximal end of the medial segment 72 abuts against the beveled distal end of the proximal segment 70. The beveled distal end of the medial segment 72 abuts against the beveled proximal end of the distal segment 74. Rotation of the medial segment 72 by 180 degrees causes the deflectable portion 14d to change from the straight configuration seen in FIG. 4A to the partially curved configuration seen in FIG. 4B. Thereafter, rotation of the distal segment by 180 degrees causes the deflectable portion 14d to change from the partially curved configuration seen in FIG. 4B to the fully curved configuration seen in FIG. 4C. It will be appreciated that this embodiment will not include a pull wire 22. Rather, the operator may rotate the medial and/or distal segments 72, 74 by hand before the guide catheter device 10d is inserted into the subject's body. Alternatively, a rotational deflection control mechanism may be provided on a portion of the device that remains outside of the body and linked to the medial and/or distal segments 72, 74 so as to enable the operator to selectively rotate the medial and/or distal segments 72, 74 after the deflectable portion 14d of the device has been inserted into the subject's body.

The deflectable guide catheters 10, 10a, 10b, 10c, 10d of this invention may be used to guide the insertion of a wide variety of devices to a variety of locations within the body. In one non-limiting example shown in FIGS. 5 and 6A-6C, the embodiment of the deflectable guide catheter 10 shown in FIGS. 1-1C is used to introduce a guidewire GW into the left maxillary sinus MS of a human subject. After the guidewire has been advanced in to the maxillary sinus MS, one or more other devices (e.g., catheters, scopes, electrodes, dilators, substance delivery implants, stents, etc.) may be advanced over the guidewire and/or through the lumen 23 of the guide catheter 20. FIG. 7 shows a dilator 100 including a balloon 100, which may be advanced over the guidewire to dilate an opening or anatomical passageway, such as the opening of a paranasal sinus. Although this particular example shows a procedure involving the maxillary sinus MS, it is to be appreciated that this is merely one example and is not intended to provide an exhaustive description of all possible procedures that may be performed using the deflectable guide catheters of this invention. Indeed, as will be well understood by persons of skill in the art, the deflectable guide catheters of this invention may be used to access the ostia of any paranasal sinuses (frontal, sphenoid, maxillary) or other passageways (e.g., openings that have been formed into the ethmoid air cell(s) or other sinuses, Eustachian tubes, naso-lacrimal ducts, etc.) and/or many other locations within the ear, nose or throat.

Figure 6A:
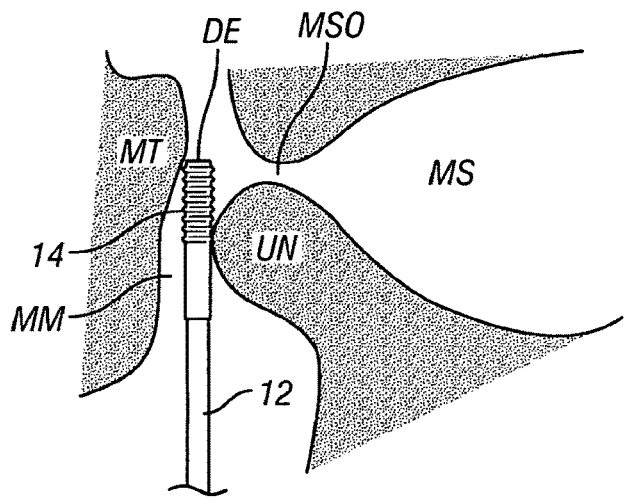
FIGS. 6A through 6C show steps in a method by which the deflectable guide catheter shown in FIG. 5 may be inserted and positioned adjacent to the ostium of the left maxillary sinus without removal or substantial modification of normal anatomical structures.
Figure 6B:
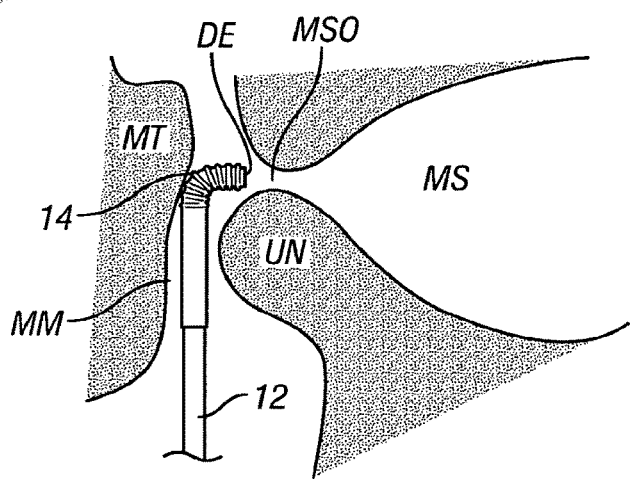
Figure 6C:
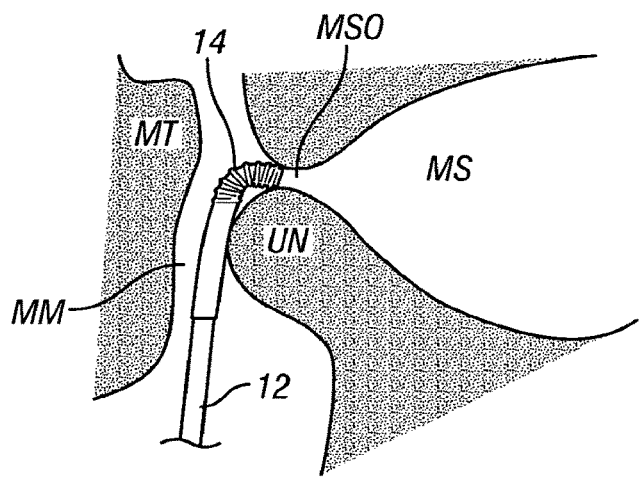

As seen in FIG. 6A, the deflectable distal portion 14 of the guide catheter 10 is initially disposed in a configuration that is substantially straight (e.g., about 0 degrees of curvature). The guide catheter shaft 12 is inserted distal end first into the subject's left nostril with the catheter shaft 12 orientated such that, when subsequently deflected, the deflectable portion 14 will curve in the lateral direction. The catheter shaft is advanced through the middle meatus MM along the lateral aspect of the middle turbinate MT until the deflectable portion 14 has passed the protruding uncinate process. Thereafter, the operator will rotatably retract the control knob 48 causing the deflectable portion 14 to curve to a configuration wherein the distal end DE of the catheter shaft 12 is directed toward the maxillary sinus ostium MSO as seen in FIG. 6B. For entry into the maxillary sinus ostium in a subject whose anatomy in this area has not been altered by prior surgery, the deflectable portion 14 will be deflected to a curve of about 90 degrees to about 110 degrees. An x-ray, fluoroscope, embedded navigation sensor useable with an image guided surgery system, the optional attached endoscope 60 (if present) or a separate endoscope (if inserted) may be used to verify that the curvature, orientation and position of the guide catheter 10 is as desired. Thereafter, the guide catheter shaft 12 may be moved in the lateral direction causing the distal end DE of the guide catheter shaft 12 to advance around the intact uncinate process UN to a location within or near the maxillary sinus ostium MSO. Thereafter, the guidewire GW is advanced through the lumen 23 of the guide catheter 10 and into the maxillary sinus MS as seen in FIG. 5. Similar procedures (but different curvatures of the deflectable portion 14) may also be used to facilitate placement of the distal end DE of the guide catheter within or adjacent to the ostia of the frontal, sphenoid or ethmoid sinuses, within or adjacent to other openings such as that of the naso-lacrymal duct or Eustachian tube and/or adjacent to man-made openings (e.g., ethmoidectomy or othmoidotomy openings into ethmoid air cells, openings into the cranium to access anatomical structures such as the pituitary gland, etc.

The deflectable guide catheters 10, 10a, 10b, 10c, 10d of this invention may provide a number of advantages over the use of guide catheters having fixed shapes. For example, the guide catheters 10, 10a, 10b, 10c, 10d of this invention may be inserted and advanced through the nasal anatomy while in a first configuration (e.g., straight or only slightly curved) thereby allowing the distal portion of the guide catheter to easily advanced though narrow or constricted regions of anatomy and/or adjacent to other devices (e.g., an endoscope) may also be inserted into the nose. Thereafter, after the guide catheter has been advanced to a desired location, the guide catheter may be deflected to a second configuration (e.g., a substantially curved shape) thereby causing or allowing the distal opening of the guide catheter 10, 10a, 10b, 10c, 10d to move into a position that is adjacent to an in alignment with a desired sinus ostium or passageway so that the intended substance or device may be delivered through the guide catheter lumen and into or through that ostium or passageway. Thereafter, the guide catheter 10, 10a, 10b, 10c, 10d may then be returned to the first configuration (e.g., straight or only slightly curved) to facilitate its withdrawal and removal from the anatomy. In this manner, the deflectable guide catheters 10, 10a, 10b, 10c, 10d of the present invention may be easier to insert/remove and may be less traumatic to the anatomy than other guide catheters having a fixed shapes. Also, when used for some procedures (e.g., balloon dilation of a paranasal sinus ostium) the deflectable guide catheters 10, 10a, 10b, 10c, 10d of the present invention may result in faster procedure times (e.g., no need to remove balloon and guidewire from the guide catheter on one side of the nostril). Additionally, the deflectable guide catheters 10, 10a, 10b, 10c, 10d of the present invention may allow hospitals, surgical centers, surgeon's offices or other locations where these procedures are performed to maintain less inventory, as a single deflectable guide catheter bay be used to replace a number of fixed shape guide catheters used in the prior art (e.g., sinus guide catheters having fixed angles of 0, 30, 70, 90 and 110 degrees may be replaced by a single deflectable guide catheter that is capable of being deflected to angles ranging from 0 to 110 degrees.)

It is to be appreciated that the invention has been described hereabove with reference to certain examples or embodiments of the invention but that various additions, deletions, alterations and modifications may be made to these examples and embodiments without departing from the intended spirit and scope of the invention. For example, any element or attribute of one embodiment or example may be incorporated into or used with another embodiment or example, unless otherwise indicated or unless doing so would render the embodiment or example unsuitable for its intended use. Also, where the steps of a method or procedure are referred to or listed in a specific order, the order of such steps may be changed unless otherwise specified or unless doing so would render the method or procedure unsuitable for its intended use. All reasonable additions, deletions, modifications and alterations are to be considered equivalents of the described examples and embodiments and are to be included within the scope of the following claims.

What is claimed is:

1. A deflectable guide catheter device comprising:
   (a) a rigid tube that includes a lumen and a distal end;
   (b) a deflectable member that includes a distal end, wherein the deflectable member extends from the distal end of the rigid tube, wherein the distal end of the deflectable member is sized to fit within a nasal cavity of a patient;
   (c) a push and pull member that is configured to be pushed or pulled by a user, wherein the push and pull member includes proximal and distal ends, wherein the distal end of the push and pull member is fixably coupled with the distal end of the deflectable member at a point proximal to a distal most tip of the deflectable member;
   (d) a deflection control configured to allow the user to form curves in the deflectable member using the push and pull member;
   (e) a body member, wherein the push and pull member is fixably coupled with the body member, wherein the body member and the push and pull member are both configured to translate relative to the rigid shaft; and
   (f) a balloon dilator that is configured to extend distally beyond the distal most tip of the deflectable member, wherein the balloon dilator is sized and configured to dilate a passageway associated with a paranasal sinus.

2. The device of claim 1, further comprising an inner jacket having an inner surface, an outer surface, and a lumen, wherein the inner jacket extends through at least a portion of the lumen of the rigid tube and a portion of the lumen of the deflectable member.

3. The device of claim 2, wherein the rigid tube includes an inner surface and an outer surface, wherein the push and pull member extends between the inner surface of the rigid tube and the outer surface of the inner jacket.

4. The device of claim 1, further comprising an outer polymeric jacket covering at least a portion of the deflectable member.

5. The device of claim 4, wherein the outer polymeric jacket comprises a tube that has been shrunken, fused, or adhered onto the deflectable member.

6. The device of claim 4, wherein the outer polymeric jacket comprises a coating applied onto the deflectable member.

7. The device of claim 1, wherein the push and pull member is coupled with the distal end of the deflectable member using solder, adhesive, or weldment.

8. The device of claim 1, wherein the deflection control includes a control knob, wherein the body member and the push and pull member are both configured to translate longitudinally relative to the control knob due to rotation of the control knob.

9. The device of claim 8, wherein the control knob is configured to be rotated in a first direction to retract proximally both the body member and the push and pull member to cause an increase of the curvature of the deflectable member.

10. The device of claim 9, wherein the control knob is configured to be rotated in a second direction that is opposite the first direction to advance distally both the body member and the push and pull member to cause a decrease of the curvature of the deflectable member.

11. The device of claim 8, wherein the control knob includes indicia associated with the control knob for indicating the degree to which the deflectable distal portion is deflected, wherein the indicia located on a portion of the device that remains outside of the body.

12. The device of claim 1, wherein the deflectable member has a length of from about 0.625 inch to about 0.75 inch, and wherein the deflectable member has an outer diameter of from about 0.100 inch to about 0.156 inch so as to be sized and configured to extend into the nasal cavity.

13. A deflectable guide catheter device comprising:
(a) a rigid tube that includes a lumen and a distal end;
(b) a deflectable member that includes a distal end, wherein the deflectable member extends from the distal end of the rigid tube;
(c) a push and pull member that is configured to be pushed or pulled by a user, wherein the push and pull member includes proximal and distal ends, wherein the distal end of the push and pull member is fixably coupled with the distal end of the deflectable member at a point proximal to a distal most tip of the deflectable member;
(d) a control knob configured to drive the push and pull member to thereby allow the user to form curves in the deflectable member, wherein the curves range from 0 degrees to 110 degrees;
(e) a body member, wherein the push and pull member is fixably coupled with the body member, wherein the body member and the push and pull member are configured to both translate longitudinally relative to the rigid shaft and, the control knob due to rotation of the control knob; and
(f) a balloon dilator that is configured to extend distally beyond the distal most tip of the deflectable member, wherein the balloon dilator is sized and configured to dilate a passageway associated with a paranasal sinus.

14. The device of claim 13, wherein the control knob is configured to be rotated in a first direction to retract proximally both the body member and the push and pull member to cause an increase of the curvature of the deflectable member, wherein the control knob is configured to be rotated in a second direction that is opposite the first direction to advance distally both the body member and the push and pull member to cause a decrease of the curvature of the deflectable member.

15. The device of claim 9, wherein the deflection control includes indicia associated with the deflection control for indicating the degree to which the deflectable distal portion is deflected, wherein the indicia located on a portion of the device that remains outside of the body.

16. A method of using a deflectable guide catheter device, the deflectable guide catheter device comprising:
(a) a rigid tube that includes a lumen and a distal end;
(b) a deflectable member that includes a distal end, wherein the deflectable member extends from the distal end of the rigid tube, wherein the distal end of the deflectable member is sized and configured to fit within a nasal cavity of a patient;
(c) a push and pull member that is configured to be pushed or pulled by a user, wherein the push and pull member includes proximal and distal ends, wherein the distal end of the push and pull member is fixably coupled with the distal end of the deflectable member at a point proximal to a distal most tip of the deflectable member; and
(d) a deflection control configured to allow the user to form curves in the deflectable member using the push and pull member, wherein the curves range from 0 degrees to 110 degrees;
the method comprising:
(a) actuating the deflection control to drive the push and pull member to thereby deflect the deflectable member; and
(b) inserting the deflectable member into a nasal cavity of a patient.

17. The method of claim 16, further comprising advancing a working member through the deflectable member into the nasal cavity of the patient.

18. The method of claim 17, the working member comprising a balloon dilator.

19. The method of claim 18, further comprising inflating the balloon dilator to thereby dilate an anatomical passageway within the nasal cavity of the patient.

20. The method of claim 1, wherein the indicia includes markings or tactilely discernable indicators.

* * * * *